United States Patent
Bilgic

(10) Patent No.: US 9,345,848 B2
(45) Date of Patent: May 24, 2016

(54) DRY POWDER INHALER

(75) Inventor: Mahmut Bilgic, Istanbul (TR)

(73) Assignee: Sima Patent ve Lisanslama Hizmetleri Ltd. Sti., Esenler/Istanbul (TR)

( * ) Notice: Subject to any disclaimer, the term of this patent is extended or adjusted under 35 U.S.C. 154(b) by 686 days.

(21) Appl. No.: 13/451,838

(22) Filed: Apr. 20, 2012

(65) Prior Publication Data

US 2012/0260917 A1 Oct. 18, 2012

Related U.S. Application Data

(63) Continuation-in-part of application No. PCT/TR2011/000091, filed on Apr. 13, 2011, and a continuation-in-part of application No. PCT/TR2011/000094, filed on Apr. 13, 2011, and a (Continued)

(51) Int. Cl.
  *A61M 15/00* (2006.01)
(52) U.S. Cl.
  CPC ....... *A61M 15/0045* (2013.01); *A61M 15/0026* (2014.02); *A61M 15/0043* (2014.02); *A61M 15/0048* (2014.02); *A61M 15/0075* (2014.02); *A61M 2202/064* (2013.01); *A61M 2206/16* (2013.01)
(58) Field of Classification Search
  CPC ............ A61M 15/00; A61M 15/0006; A61M 15/0008; A61M 15/0025; A61M 15/0026; A61M 15/0031; A61M 15/0033; A61M 15/0036; A61M 15/0041; A61M 15/0043; A61M 15/0045; A61M 15/0048; A61M 15/0051; A61M 15/0055; A61M 15/006; A61M 15/007; A61M 15/0086; A61M 15/0091; B65D 75/28; B65D 75/327; B65D 75/34

USPC .............. 128/200.24, 203.12, 203.15, 203.21
See application file for complete search history.

(56) References Cited

U.S. PATENT DOCUMENTS

| | | | |
|---|---|---|---|
| 6,092,522 A | 7/2000 | Calvert et al. | |
| 6,234,365 B1 | 5/2001 | Bougamont et al. | |
| 6,880,555 B1* | 4/2005 | Brunnberg et al. | ...... 128/203.12 |
| 2002/0132001 A1 | 9/2002 | Garthwaite et al. | |
| 2003/0172927 A1* | 9/2003 | Young et al. | ............. 128/203.15 |
| 2004/0094152 A1 | 5/2004 | Harvey et al. | |
| 2005/0005934 A1 | 1/2005 | Harvey | |

(Continued)

FOREIGN PATENT DOCUMENTS

| | | |
|---|---|---|
| EP | 1175220 A2 | 1/2002 |
| EP | 2082759 A1 | 7/2009 |

(Continued)

OTHER PUBLICATIONS

International Search Report and Written Opinion for International Application No. PCT/TR2011/000085 dated Aug. 10, 2011 (10 pages).

(Continued)

*Primary Examiner* — Annette Dixon
(74) *Attorney, Agent, or Firm* — Clark & Elbing LLP

(57) ABSTRACT

The present invention relates to an inhaler which is appropriate for delivery of medicament in dry powder form used in respiratory diseases, particularly in asthma and chronic obstructive pulmonary disease (COPD). In addition, the present invention relates to an inhaler which includes a blister package appropriate for carrying the medicament in dry powder form and used to realize an effective inhalation.

2 Claims, 29 Drawing Sheets

Related U.S. Application Data continuation-in-part of application No. PCT/TR2011/000089, filed on Apr. 13, 2011, and a continuation-in-part of application No. PCT/TR2011/000093, filed on Apr. 13, 2011, and a continuation-in-part of application No. PCT/TR2011/000085, filed on Apr. 13, 2011, and a continuation-in-part of application No. PCT/TR2011/000088, filed on Apr. 13, 2011, and a continuation-in-part of application No. PCT/TR2011/000087, filed on Apr. 13, 2011, and a continuation-in-part of application No. PCT/TR2011/000095, filed on Apr. 13, 2011, and a continuation-in-part of application No. PCT/TR2011/000086, filed on Apr. 13, 2011, and a continuation-in-part of application No. PCT/TR2011/000090, filed on Apr. 13, 2011, and a continuation-in-part of application No. PCT/TR2010/000210, filed on Oct. 20, 2010.

(56) References Cited

U.S. PATENT DOCUMENTS

| | | | |
|---|---|---|---|
| 2005/0154491 | A1 | 7/2005 | Anderson et al. |
| 2005/0172964 | A1 | 8/2005 | Anderson et al. |
| 2005/0268909 | A1 | 12/2005 | Bonney et al. |
| 2006/0196504 | A1 | 9/2006 | Augustyn et al. |
| 2007/0062525 | A1 | 3/2007 | Bonney et al. |
| 2008/0196718 | A1* | 8/2008 | Connell et al. ........... 128/203.15 |
| 2008/0308102 | A1 | 12/2008 | Davies et al. |
| 2009/0078252 | A1 | 3/2009 | Anderson et al. |
| 2009/0139516 | A1 | 6/2009 | Augustyn et al. |
| 2009/0188498 | A1* | 7/2009 | Thoemmes ....... A61M 15/0045 128/203.21 |
| 2010/0000528 | A1 | 1/2010 | Palmer et al. |
| 2010/0000529 | A1 | 1/2010 | Prime et al. |
| 2010/0059052 | A1 | 3/2010 | Davies et al. |
| 2014/0318538 | A1 | 10/2014 | Bilgic |

FOREIGN PATENT DOCUMENTS

| | | |
|---|---|---|
| EP | 2082764 A1 | 7/2009 |
| GB | 1459426 A | 12/1976 |
| GB | 2407042 A | 4/2005 |
| GB | 2447560 A | 9/2008 |
| WO | WO-00/33847 A1 | 6/2000 |
| WO | WO-01/41770 A2 | 6/2001 |
| WO | WO-02/36189 A1 | 5/2002 |
| WO | WO-03/095010 A2 | 11/2003 |
| WO | WO-2006/066908 A1 | 6/2006 |
| WO | WO-2007/012960 A1 | 2/2007 |
| WO | WO-2008/074098 A1 | 6/2008 |
| WO | WO-2009/003989 A1 | 1/2009 |
| WO | WO-2009/139731 A1 | 11/2009 |

OTHER PUBLICATIONS

International Search Report and Written Opinion for International Application No. PCT/TR2011/000086, mailed Oct. 6, 2011 (8 pages).
International Search Report and Written Opinion for International Application No. PCT/TR2011/000087 mailed Aug. 18, 2011 (8 pages).
International Search Report and Written Opinion for International Application No. PCT/TR2011/000088 mailed Oct. 6, 2011 (8 pages).
International Search Report and Written Opinion for International Application No. PCT/TR2011/000089 mailed Jul. 22, 2011 (9 pages).
International Search Report and Written Opinion for International Application No. PCT/TR2011/000090 mailed Aug. 22, 2011 (8 pages).
International Search Report and Written Opinion for International Application No. PCT/TR2011/000091 mailed Jul. 29, 2011 (9 pages).
International Search Report and Written Opinion for International Application No. PCT/TR2011/000093 mailed Jul. 21, 2011 (9 pages).
International Search Report and Written Opinion for International Application No. PCT/TR2011/000094 mailed Sep. 28, 2011 (9 pages).
International Search Report and Written Opinion for International Application No. PCT/TR2011/000095 mailed Aug. 4, 2011 (9 pages).
International Search Report and Written Opinion for International Application No. PCT/TR2011/000210 mailed Mar. 7, 2012 (7 pages).

* cited by examiner

DRY POWDER INHALER

CROSS-REFERENCE TO RELATED APPLICATIONS

This application is a continuation-in-part of PCT application No. PCT/TR2010/000210, filed Oct. 20, 2010, and PCT application Nos. PCT/TR2011/000085, PCT/TR2011/000086, PCT/TR2011/000087, PCT/TR2011/000088, PCT/TR2011/000089, PCT/TR2011/000090, PCT/TR2011/000091, PCT/TR2011/000093, PCT/TR2011/000094, and PCT/TR2011/000095, filed Apr. 13, 2011, each of which is incorporated herein by reference in its entirety. This application also claims priority to Turkish patent applications TR2009/07917, filed Oct. 20, 2009, TR2010/02877, filed Apr. 13, 2010, TR2010/03091, filed Apr. 20, 2010, TR2010/03238, filed Apr. 26, 2010, TR2010/04307, TR2010/04308, TR2010/04310, TR2010/04312, TR2010/04313, and TR2010/04317, filed May 28, 2010.

BACKGROUND OF THE INVENTION

It is rather common to use inhalers for delivering medicaments utilized in the treatment and prophylaxis of respiratory diseases. Inhalation treatment is the most commonly preferred treatment method in these diseases as the inhalers provide ease of use; the medicaments have rapider onset of time resulting from local administration and they have fewer side effects. Various inhalers have been designed in order to provide effective and sufficient delivery of the medicaments used in the treatment of respiratory diseases, particularly in asthma and chronic obstructive pulmonary disease. These inhalers vary according to their operating mechanisms and the physical form of the medicament to be delivered.

In the inhalers used to deliver the medicaments in dry powder form, the medicament is carried in reservoirs, capsules or blisters packages. It is highly significant to deliver each dose to the patient with exact accuracy and preciseness since the required medicament dose in the inhalation is very low.

In general, one blister pocket containing medicament in dry powder form is opened in response to each actuation of the device in inhalers comprising blister packages. One blister pocket containing one dose of dry powder medicament is usually opened by peeling the blister package indexed upon the actuation of the device or piercing the blister pocket by the piercing means in the inhaler. The inhalers comprising peelable blister packs enable the sufficient amount of the dry powder medicament contained in the opened blister to be easily inhaled as the airflow enters the opened blister pocket more easily in the inhalers comprising peelable blister packs than the inhalers comprising pierceable blister packs. Therefore, the blister package should be indexed enough to enable the blister pocket to be opened completely so as to realize an effective inhalation in response to each actuation of the inhaler. However, it is quite difficult to enable the blister package to be indexed properly to the same extent in each actuation of the device so as to realize a safe inhalation in the inhaler comprising peelable blister packages. In the case that the blister package that is indexed upon the actuation of the device is indexed less than the required extent, the blister pocket may not be opened completely while more than one blister pocket may be opened in the case that the blister package is indexed more than the required extent. The fact that one blister pocket cannot be opened completely and an effective inhalation cannot be realized as the sufficient amount of the active agent comprised in the dry powder medicament cannot be delivered to the patient or more than the required amount of the active agent is delivered to the patient as one blister pockets are opened lead to dangerous consequences. Therefore, controlled dosing of the medicament in dry powder form cannot be achieved when the blister package is not indexed properly to the same extent in response to each actuation of the inhaler.

The inhalation device marketed under the trade mark Diskus® by GlaxoSmithKline is one of the most well-known inhalers on the market. This device operates with a slide mechanism and a blister strip package in which the dry powder medicament is carried. However, this device needs to be improved in terms of specifications to enable the blister package to be properly indexed to the same extent in response to each actuation of the device.

The inventor has surprisingly found that the force of attraction imposed by the winding wheel on the lid sheet is balanced, and thus the blister package is properly indexed to the same extent in response to each actuation of the device in the case that each of the preferably polyoxymethylene resilient wings of the winding wheel, on which the lid sheet of the blister package peeled upon the actuation of the inhaler is coiled, is composed of three parts in the inhaler comprising peelable blister package.

To this respect, the present invention relates to an inhaler comprising peelable blister package appropriate for delivering dry powder medicament which enables the blister package to be indexed properly to the same extent in response to each actuation of the inhaler.

DETAILED DESCRIPTION OF THE INVENTION

The dry powder inhaler in accordance with the present invention, which is devised to achieve an effective inhalation, consists of the mechanical components. Said dry powder inhaler comprises a housing on which the mechanical components which are required to achieve an effective inhalation of the dry powder medicament, are located. These mechanical components constitute the dispensing mechanism which is actuated as a result of the movement of the mouthpiece cover.

All the mechanical components of the dispensing mechanism is located in the housing which can be in any suitable shape, preferably circle or oval, to provide for working of these mechanical components properly and for interaction of the mechanical components with one another properly.

According to the invention, the dispensing mechanism which causes the advancement of the blister strip, interacts with directly to the mouthpiece cover through the center of the dry powder inhaler and comprises the gear mechanism of the dry powder inhaler. The dispensing mechanism is actuated by the fact that the movement of the mouthpiece cover is transmitted to the dispensing mechanism via a central hub gear of the dispensing mechanism. So that, before the inhalation of the dry powder inhaler, the single movement which is the movement of the mouthpiece cover from one position to another position, results in that the mouthpiece is completely uncovered, the peelable blister strip is advanced by working of the dispensing mechanism for inhaling the dry powder medicament from the blister and the dose counter shows the number of doses left to be taken. Therefore, the patients from every age, can use the dry powder inhaler in accordance with the present invention easily and inhale the dry powder medicament fastly and effectively.

Figure 1A:
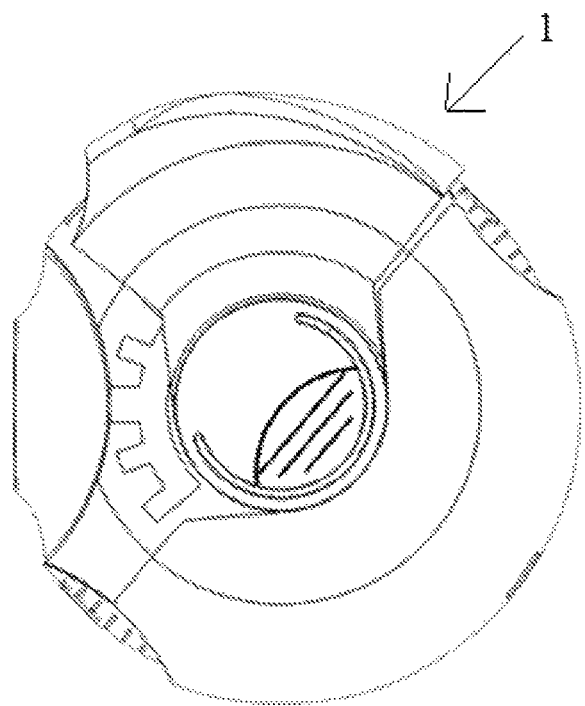
FIG. 1a is a perspective view of the inhaler according to the present invention.
Figure 1B:
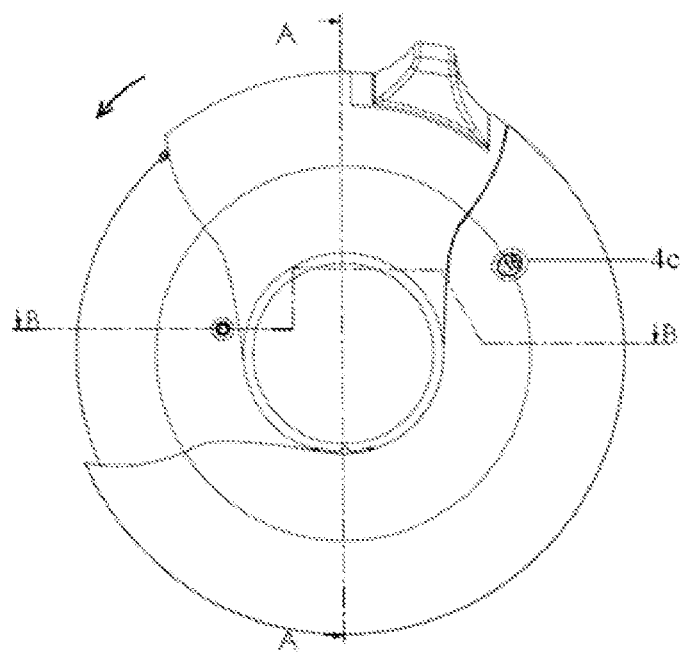
FIG. 1b is another perspective view of the inhaler according to the present invention.
Figure 1C:
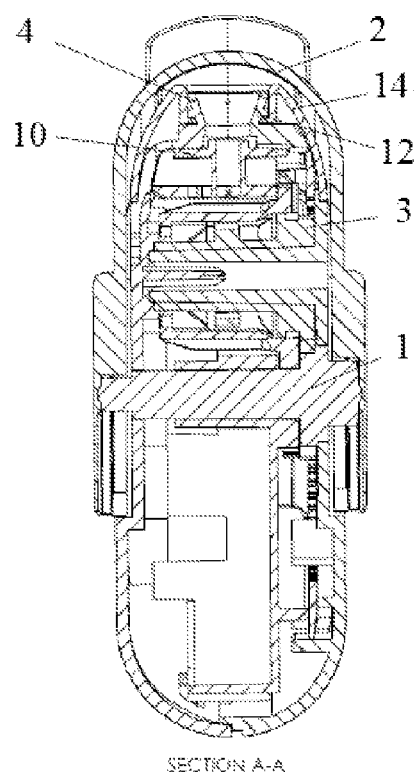
FIGS. 1c and 1d are views of the A-A and B-B cross sections of the inhaler of the present invention, respectively.
Figure 1D:
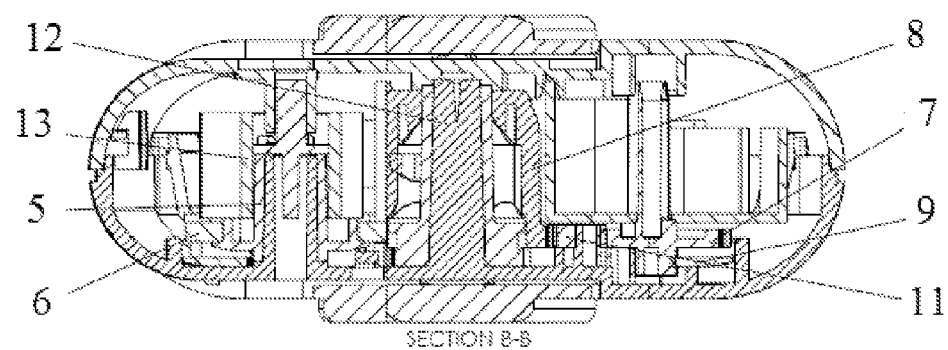
Figure 2A:
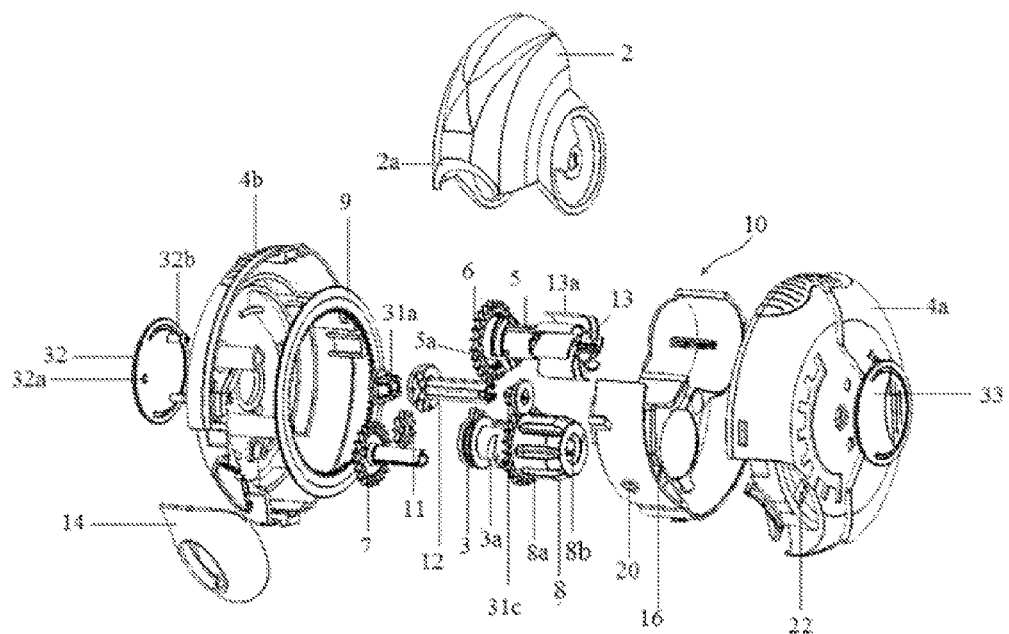
FIG. 2a is an exploded view of the inhaler according to the invention.
Figure 2B:
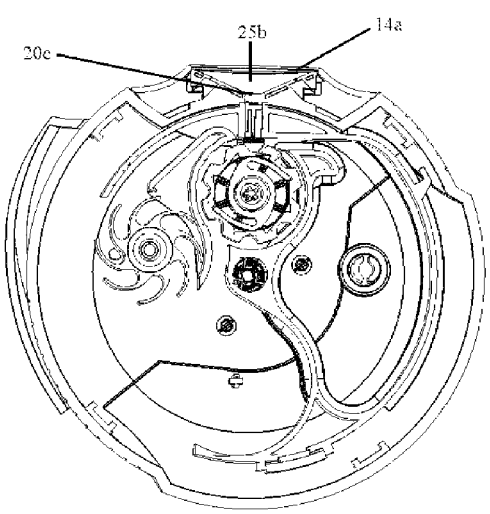
FIG. 2b is a vertical cross-sectional view of the inhaler according to the present invention.

The inhaler (1) pertaining to the present invention comprises a gear mechanism situated in the housing (10) between the upper housing member (4a) and the lower housing member (4b) in order to enable the inhalation of the dry powder medicament carried in a blister package (15) as displayed in FIGS. 1a and 2a. Each component of the inhaler (1) is positioned at suitable spots on the housing (10) to guarantee their working properly and accurately. The cross-sectional view A-A in FIG. 1c and the cross-sectional view B-B of FIG. 1d clearly display the communication of the gear mechanism with the other components of the inhaler (1) and their locations.

Another aspect of the invention, the mouthpiece cover is present in only two positions: the first position in which the mouthpiece is completely covered for protection of this mouthpiece, the second position in which the mouthpiece is completely uncovered, the mouthpiece can be cleaned easily and the dry powder medicament can be inhaled through the mouthpiece.

The dry powder inhaler in accordance with the present invention has a holder on the movable mouthpiece cover. This holder can be in any suitable form which makes the patients move the mouthpiece cover easily. Therefore, the mouthpiece cover can be moved easily by holding this holder on the mouthpiece cover.

The inhaler (1) pertaining to the present invention shown in FIGS. 1a and 2a is ready for inhalation. In this case, the mouthpiece cover (2) is in the second position and the mouthpiece (14) is entirely exposed. The mouthpiece cover (2) has to be rotated by holding on the carved part (2a) on one end of the mouthpiece cover (2) in order to switch to the second position from the first position wherein the mouthpiece is completely covered. In this way, the mouthpiece (14) is completely exposed when the mouthpiece cover (2) is switched to the second position from the first position and the gear mechanism is triggered by the drive gear (12). The drive gear (12) precisely transmits the movement of the mouthpiece cover (2) to the indexing ratchet wheel (3).

According to the invention, the indexing/advancement of the peelable blister strip is achieved by a rotatable index wheel. This rotatable index wheel having recesses therein, is engageable with the peelable blister strip in use with said dry powder inhaler such that said recesses each receive a respective cavity of the base sheet of a blister strip in use with said dry powder inhaler. The index gear interacting with the index wheel can be provided with a stopper or a lock shaft to provide irreversible rotation of the peelable blister strip. Because of the fact that the stopper engages the index gear interacting with the index wheel after the advancement of the peelable blister strip, the peelable blister strip is present at a certain position wherein one blister is opened completely and the dry powder medicament in this blister can be inhaled by the patient. In each actuation of the dispensing mechanism, the index wheel rotates irreversibly with the same angle, so that, open blister of the blister strip is situated in correct and accurate position for inhaling the effective amount of the dry powder medicament from open blister with high discharging capacity.

According to the present invention, the dry powder inhaler in which the index gear and the other gears interacting with the index gear directly or indirectly engage with one another correctly so that the dispensing mechanism works properly for delivering effective amount of the dry powder medicament to the lungs in each inhalation. It is important that the engagement especially between the gear of the index wheel and central hub gear is proper and tight because of the fact that the movement of the mouthpiece cover, which causes the actuation of the dispensing mechanism, is transmitted to the index gear in the dispensing mechanism via central hub gear.

The peelable blister strip, which consists of the blisters wherein each of the blisters has one dose of the dry powder medicament, is hold as winding up around itself in the blister strip chamber of the dry powder inhaler and is in elongate form. A base sheet and lid sheet of the peelable blister strip are peeled apart from each other to open a blister for inhaling the dry powder medicament contained by it. The actuation of the dispensing mechanism as a result of the movement of the mouthpiece cover leads to advancement of the blister. While the peelable blister strip is advanced by actuating the dispensing mechanism, the base sheet and the lid sheet of the peelable blister strip are peeled apart from each other to open one blister and the dry powder medicament in open blister become ready for inhalation in the opening station.

Another aspect of the present invention, the base sheet and the lid sheet of the peelable blister, which are peeled apart from each other while the peelable blister strip is advanced, gather in separate parts of the inhaler. The lid take-up mechanism comprises a wheel around which the lid sheet is wound tightly and it uses torsional force on the lid sheet for pulling apart the lid sheet from the base sheet of the blister that has been received at the opening station in which the dry powder medicament is inhaled from open blister. The base sheet, in which blisters are formed to define blister pockets (cavities) therein for containing distinct medicament dose portions, is wound around the base sheet take-up spindle which is hold in another part of the housing.

Various known techniques can be employed to join the lid and base sheet and hence to seal the blisters of the peelable blister strip. Such methods include adhesive bonding, hot metal bonding, hot metal welding, radio frequency welding, laser welding, ultrasonic welding and hot bar sealing. The lid sheet and base sheet of the peelable blister strip are particularly sealable by 'cold form' sealing methods, which are conducted at lower temperatures than conventional heat sealing methods. Such 'cold form' sealing methods are of particular utility where the medicament or medicament formulation for containment within the blister is heat sensitive.

The lid sheet and the base sheet of the peelable blister strip, consists of many layers which constitute the lid sheet and the base sheet of the blister strip such as polymeric layer, aluminum foil and optionally Aclar® fluoropolymer film.

Aclar® fluoropolymer film is a polymeric film which is used for production of the blister strip and provides high moisture protection. This chemically inert film does not cause any change in taste of the formulation when it is in contact with the dry powder formulation. It easily forms a lamellar structure with other polymeric layers which are made from various polymers. It is suitable for treatment with heat.

Desiccant agents are optionally added to the polymeric layers in order to reduce moisture and gas permeability of the polymeric layers for protection of stability of the dry powder formulation contained in the blisters which are juxtaposed on the peelable blister strip. Some examples of the desiccant agents are silica gel, zeolite, alumina, bauxsite, anhydrous calcium sulfate, activated carbon, clay capable of absorbing water.

According to the invention, aluminium foil is used both in the lid sheet and in the base sheet of the peelable blister strip to provide high humidity and gas protection because of that aluminium foil is conventionally used in both the lid sheet and the base sheet of the blister strip for high humidity and gas protection. These layers must have the sufficient thickness which provides the protection for the stability of humidity sensitive dry powder formulation which is carried in the blister cavity. Because of this reason, the thickness of aluminium foil that is used in the lid sheet and the base sheet of the blister strip is in the range of 10 to 40 µm, preferably of 15 to 30 µm.

The polymeric layers which are contained in the lid sheet and the base sheet of the peelable blister strip in accordance with the present invention may be made from either same or different polymers. The thickness of these polymeric layers depends on the type of polymeric substance used and its properties. Therefore, the thickness of each polymeric layer which is used in the lid sheet and the base sheet of said blister strip is in the range of 15 to 60 µm, preferably of 20 to 35 µm depending on the type of polymer used.

The inside layer of blister cavity of said blister strip which is in contact with dry powder formulation is polymeric layer because of the fact that aluminium foil causes adhesion of a part of dry powder formulation to inside layer of the cavity due to electrostatic forces, and hence cause uncontrolled dosing.

According to the present invention, the polymers used for forming polymeric layers are preferably selected from a group comprising thermo-plastic polymers such as polyethylene, polypropylene, polystyrene, polyolefin, polyamide, polyvinyl chloride, polyurethane, or synthetic polymers.

Moreover, said blisters which are placed on the peelable blister strips mentioned above, can be in any appropriate shape. Blisters that are placed to the bottom sheet of the blister strip can be in the same or different shapes and volumes and depending on the type of treatment can comprise dry powder medicament in the same or different amounts.

Figure 3:
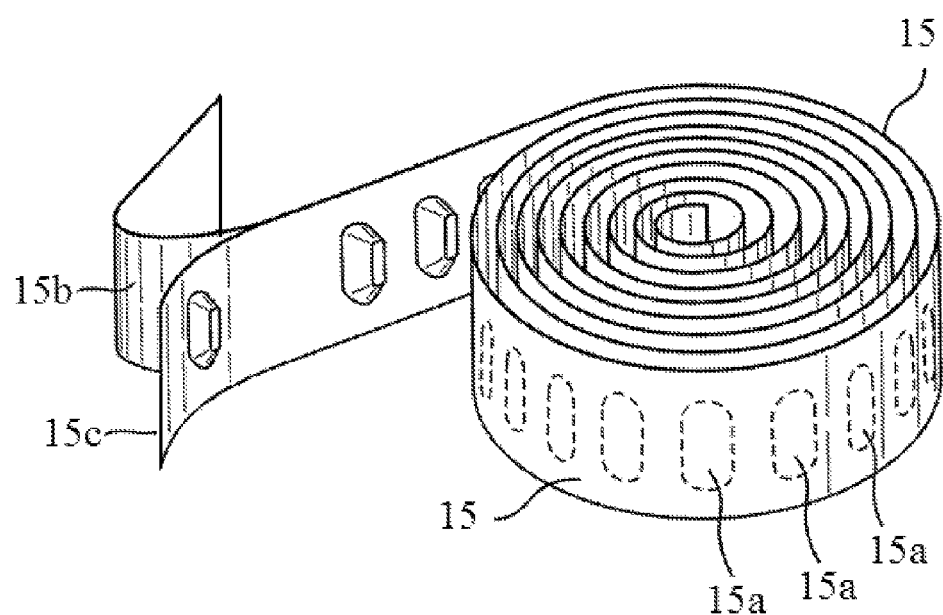
FIG. 3 is a perspective view of the blister pack for use with the inhaler according to the invention.

The indexing wheel (8) which engages with the indexing ratchet wheel (3) enables the blister package (15) shown in FIG. 3 to be indexed. The blister pockets (15a) composing the blister package are received in the recesses (8a) on the indexing wheel and the blister package (15) is indexed when the indexing wheel (8) rotates. In the inhaler pertaining to the present invention, shapes of the recesses (8a) on the indexing wheel (8) have been designed to match the shapes of the blister pockets (15a) composing the blister package (15) for the blister package to be indexed properly.

The blister package (15) shown in FIG. 3 is composed of the lid sheet (15b) which provides impermeability and the base sheet (15c) on which the blister pockets (15a) are spaced at equal intervals. Each blister pocket contains medicament in dry powder form comprising one or more active agents.

The rotational movement that the mouthpiece cover (2) of the device executes while switching from the first position to the second is transmitted to the indexing ratchet wheel (3) via the drive gear (12) that the mouthpiece cover (2) engages with. As displayed in FIG. 2a, arms (3a) of the indexing ratchet wheel interlocks with protrusions inside the indexing wheel (8) and rotates the indexing wheel (8) unidirectionally. Therefore, the blister package (15) is indexed forward while the indexing wheel (8a) rotates as the blister pockets (15a) composing the blister package (15) are received in the recesses (8a) of the indexing wheel. The beak (16) in the housing (10) provides the blister package (15) to be peeled while the blister package (15) is indexed and provides one blister pocket (15a) to be opened in response to each actuation of the inhaler (1).

The winding wheel gear (6), which is another component of the gear mechanism, engages with the indexing wheel (8) as displayed in FIG. 2a. The mechanism gear (5) that interlocks with the winding wheel (13) from inside has arms (5a) to interlock with the interior teeth of the winding wheel gear (6). When the indexing wheel (8) rotates the winding wheel gear (6), the winding wheel rotates unidirectionally owing to the arms of the mechanism gear (5a) which interlocks with the interior teeth of the winding wheel gear (6) and the lid sheet (15b) which is peeled away while the blister package is indexed is tightly coiled on the resilient wings (13a) of the winding wheel. The base sheet (15c) of the blister package (15) where the blister pockets are spaced is accumulated in a separate part (18a) of the device (FIG. 4j). Each resilient wing (13a) of the winding wheel extends from the center of the winding wheel (13) to the end.

Figure 12:
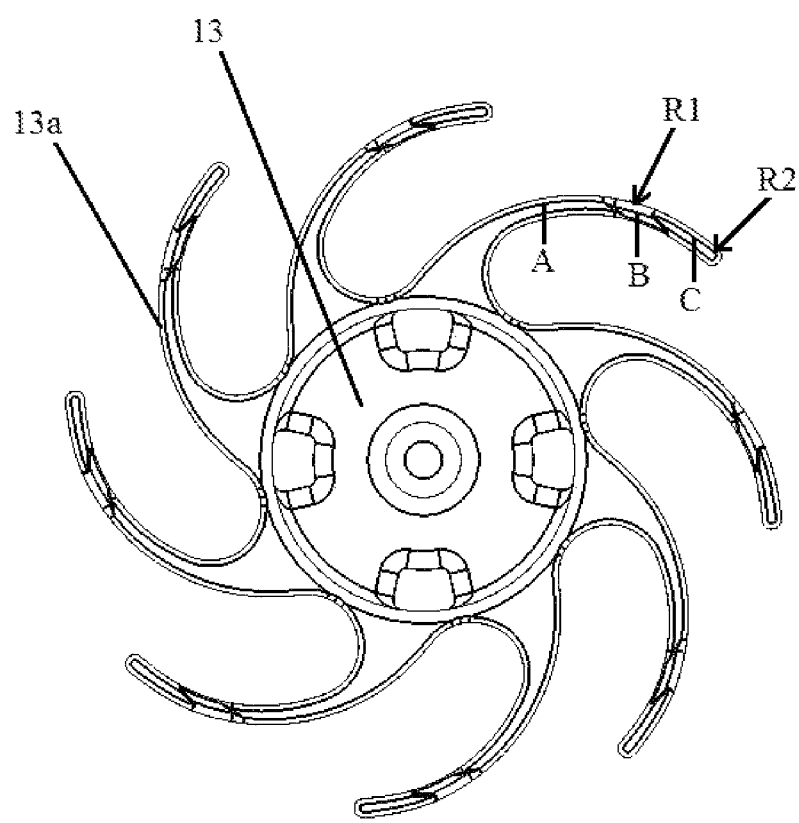
FIG. 12 is a perspective view of the winding wheel pertaining to the present invention.

As illustrated in FIG. 12, the winding wheel (13) of the inhaler pertaining to the present invention is composed of a plurality of resilient wings which are preferably made of polyoxymethylene plastics. Each of these resilient wings (13a) is composed of three parts (A, B, C) each of which has different radius values. Thus, these resilient wings (13a) stretch enough to balance the force of attraction imposed on the lid sheet (15b) of the blister package, therefore on the blister package (15), as the thickness of the lid sheet (15b) of the blister package coiling on them increases, and they enable the blister package (15) to be indexed properly to the same extent in response to each actuation of the inhaler. The resilient wings of the winding wheel illustrated in FIG. 12 are composed of 3 parts (A; B; C). The average radius (R1) of the second part (B) of each resilient wing is in the range of 4.60 mm to 5.20 mm, preferably in the range of 4.75 mm to 5.15 mm; and the radius (R2) of the piece of the third part (C) that curls through the end of the resilient wing is in the range of 0.9 mm to 1.70 mm, preferably in the range of 1.10 mm to 1.50 mm.

Figure 4A:
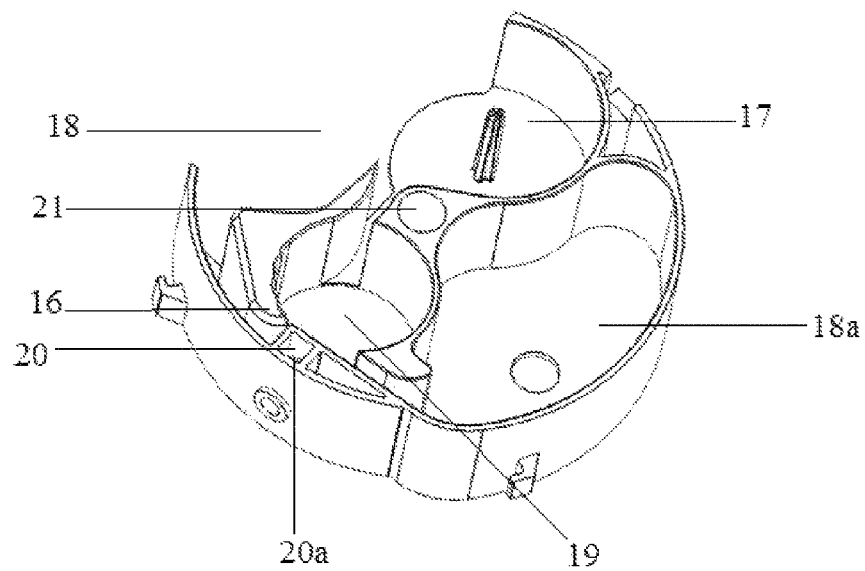
FIGS. 4a and 4b are perspective views of the housing of the inhaler according to the invention.
Figure 4B:
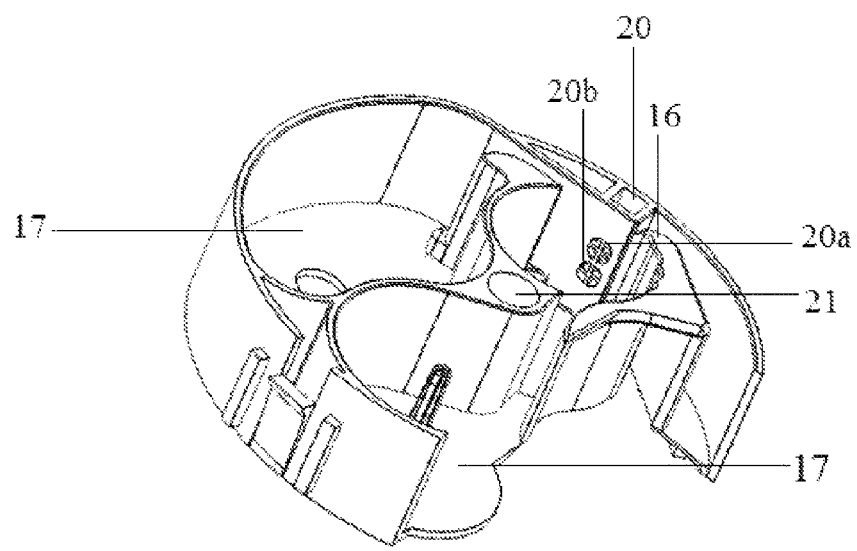

Different views of the housing (10) wherein the gear mechanism and the other components of the inhaler (1) pertaining to the present invention are arranged are displayed in FIGS. 4a and 4b. Furthermore, as can be seen in FIGS. 4a through 4j, the housing (10) also comprises the components having significant roles in the actuation of the device such as the beak (16), the manifold (20), the apertures with four sub-apertures (20a, 20b). Each component comprised in the housing is situated in appropriate parts of the housing (10) in order to enable the inhaler (1) to work properly. The drive gear (12) passes through the center (21) of the housing and joins the mouthpiece cover (2) at both sides of the inhaler. The blister package (15) is in the lower part (17) of the housing as coiled up. In response to each actuation of the inhaler (1), the blister package (15) is peeled by the beak (16) in the housing while being indexed by the indexing wheel (8) situated in the upper part (19) of the housing. The lid sheet (15b) of the blister package (15) which provides impermeability is indexed over the beak (16) and coiled on the winding wheel (13) which is situated in the side part (18) of the housing. The base sheet (15c) of the blister package (15) on which the blister pockets (15a) are spaced, on the other hand, is accumulated in the separated compartment (18a) of the housing (10). Upon the inhalation of the patient, the air passes through the air inlet with four sub-apertures (20a) under the manifold (20) into the opened blister pocket; entrains the dry powder medicament contained in the opened blister pocket (15a) in response to each actuation of the device; provides it to pass through the other aperture with four-sub-apertures (20b) and reach the mouthpiece via the manifold (20).

The housing (10) and the other components of the inhaler (1) pertaining to the present invention are stably kept together as the upper housing member (4a) and the lower housing member (4b) displayed in FIGS. 5a through 5h are joined together. The engagement tabs (28) on the inside surface of the lower housing member (4b) engage with the engagement recesses (27) on the inside surface of the upper housing member (4a) and the upper and lower housing members are fixed tightly. Therefore, the protrusions (23a, 23b) on the upper housing member (4a) and the protrusions (24a, 24b) on the lower housing member (4b) are joined end to end and they define the restricted path for the rotational movement of the mouthpiece cover (2). The mouthpiece cover (2) can be moved along this path. When the mouthpiece cover (2) is on the first position, the mouthpiece is completely covered, the device is in standby mode and the mouthpiece cover (2) leans on the first protrusion (23a) on the upper housing member and the first protrusion (24a) on the lower housing member. The mouthpiece (14) is manually slid along the rotational path with the help of the carved part to switch to the second position. The mouthpiece is completely exposed when the cover is in this position, one dose of the dry powder medicament is ready for inhalation and the mouthpiece cover (2) leans on the second protrusion (23b) on the upper housing member and the second protrusion (24b) on the lower housing member.

In opening station of the dry powder inhaler in accordance with the invention, there is a beak, and the lid sheet and the base sheet are separable by peeling to open a blister cavity about this beak. After the blister cavities passes through the opening station, because of the engagement between recesses of the index wheel and blister cavities, the blister strip, which has been advanced as a result of the actuation of the dispensing mechanism, is positioned correctly and accurately in the dispensing station for achieving the effective inhalation of the dry powder formulation. An airflow, which enters to the dry powder inhaler throughout at least an airflow inlet during the inhalation of the patient through the dry powder inhaler, reaches to the dry powder medicament in the cavity of open blister in the dispensing station. Said dry powder medicament is drawn out through manifold of the dry powder inhaler and then it is delivered to the patient by the airflow. The airflow inlet can be in any suitable shape which provide for entering of airflow to the dry powder inhaler easily.

According to the invention, the manifold through which the dry powder medicament is drawn out by the airflow, can be in any suitable form which enables delivery of the dry powder medicament to the patient in an effective way.

Figure 4C:
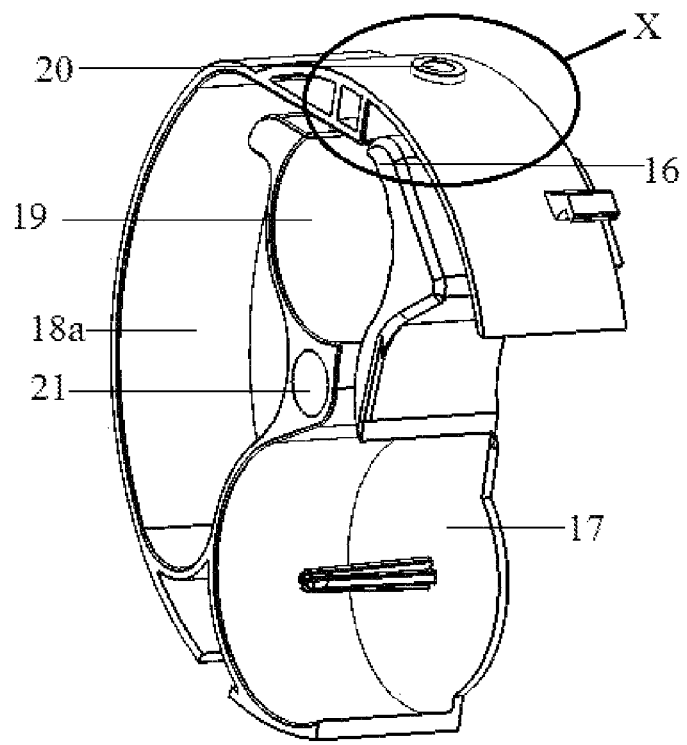
FIG. 4c is another perspective view of the housing of the inhaler according to the invention.
Figure 4D:
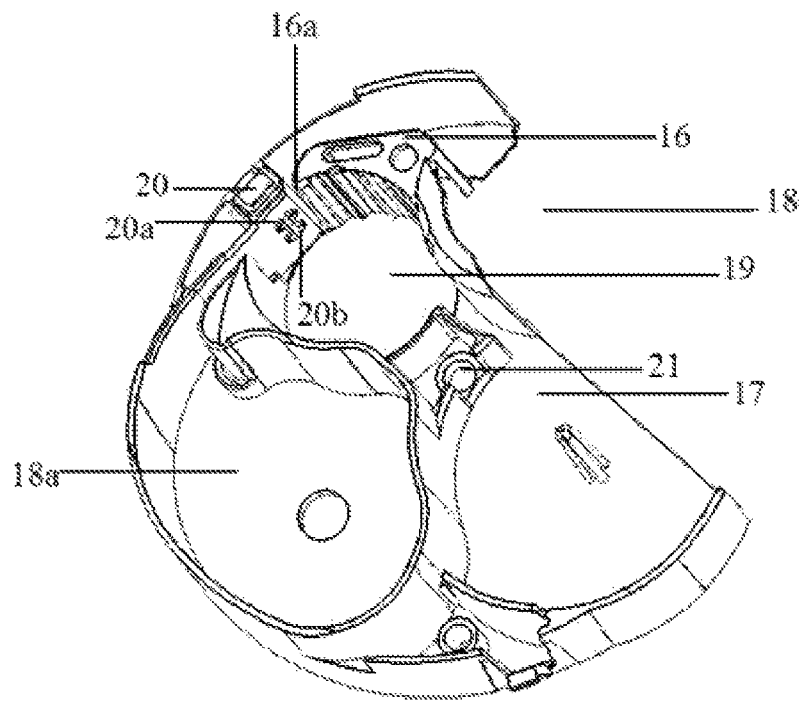
FIG. 4d is another perspective view of the housing of the inhaler of the invention.
Figure 4E:
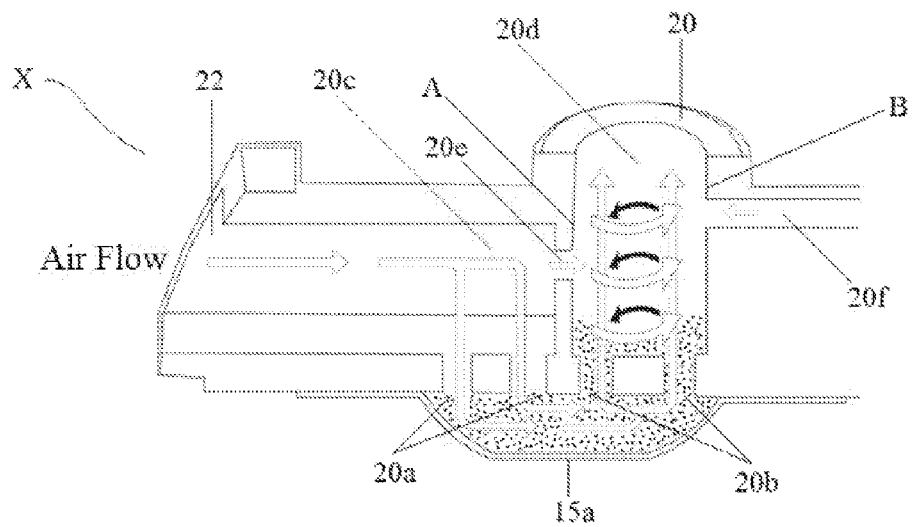
FIGS. 4e and 4f are cross-sectional views of the manifold part of the inhaler pertaining to the invention which is shown as X in FIG. 4c.
Figure 4F:
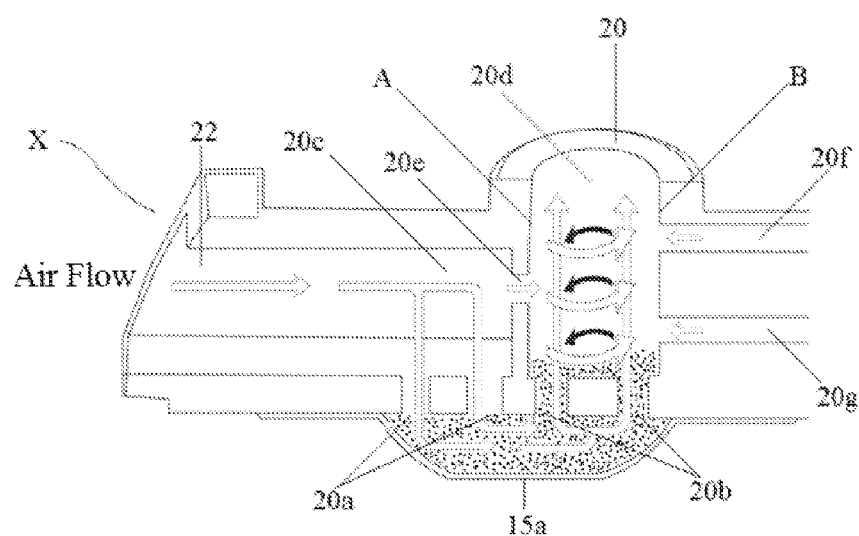
Figure 4G:
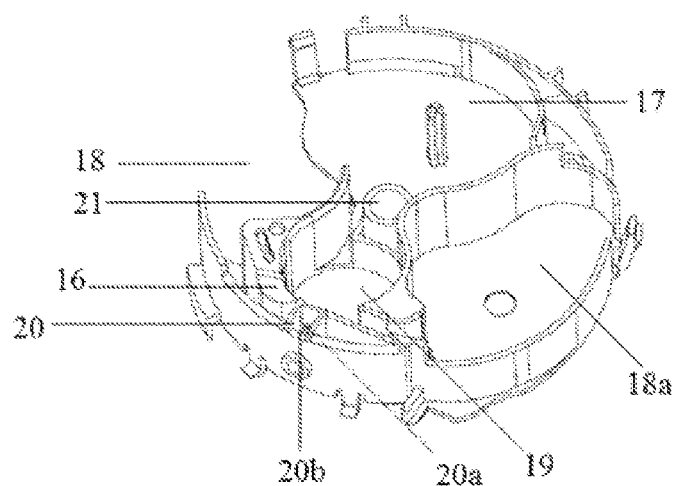
FIGS. 4g and 4h are perspective plan and bottom views of the housing of the inhaler according to the invention, respectively.
Figure 4H:
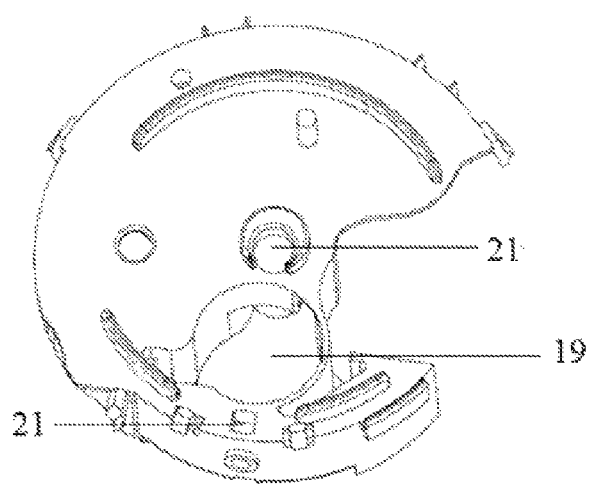

A view of the cross-section of the housing (10) which illustrated as X in FIG. 4c and includes the manifold (20) is given in FIGS. 4e and 4f. According to FIG. 4e, the blister pocket (15a) opened upon the actuation of the inhaler (1) is positioned immediately under the apertures with four sub-apertures (20a, 20b). There are two apertures with four sub-apertures (20a, 20b) on the edge of the manifold (20) which is close to the blister (15a) and they are partitioned off from each other by a wall. This wall is named as wall A in FIG. 4c and it partitions the manifold (20) into two parts. Wall A lies between the first part (20c) and the second part (20d) of the manifold and it belongs to both the first part (20c) and the second part (20d) of the manifold. Upon the respiration of the patient so as to inhale the medicament in dry powder form in the opened blister pocket (15a), the external air that enters the inhaler passing through the air inlet (22) on the upper housing member reaches the first part (20c) of the manifold. Some part of this airflow reaches the opened blister (15a) by passing through the aperture with four sub-apertures (20a) on the edge of the first part of the manifold. The airflow reaching the opened blister pocket (15a) entrains the dry powder medicament in the blister to the second part (20d) of the manifold through the other aperture with four sub-apertures (20b) on the edge of the manifold which is close to the blister. Wall A and wall B shown in FIG. 4c are two opposite walls in the second part (20d) of the manifold. Some part of the external air which runs through the air inlet (22) and enters the inhaler (1) upon the patient's breathing in passes through the first part (20c) of the manifold and reaches the opened blister pocket (15a) while the rest passes through the aperture (20e) on wall A and the aperture (200 on wall B and enters the second part (20d) of the manifold. The apertures (20e, 200 on wall A and wall B are asymmetrically positioned. Shapes and the cross-sections of the apertures (20e, 200 on wall A and wall B can be identical or different. Thus, an effective turbulence is created in the second part (20d) of the manifold as the speed of the airflow entering through the aperture (20e) on wall A and the speed of the airflow entering through the aperture (200 on wall B are different. The created turbulence disperse the agglomeration of the dry powder medicament entrained to the second part (20d) of the manifold and provides the dry powder medicament to be delivered to the patient at appropriate particle size distribution.

Another cross-sectional view of the part of the housing which is shown as X in FIG. 4c is given in FIG. 4f. In the cross-sectional view of the manifold illustrated in FIG. 4f, there are two apertures (20f, 20g) on wall B of the manifold differently from FIG. 4e. The apertures (20e, 20f) on wall A and wall B are asymmetrically positioned with respect to each other. The shapes and the cross-sections of the apertures (20e, 20f, 200 on wall A and wall B which allow the air in the second part (20d) of the manifold can be identical or different. Thus, the airflow entering in through the aperture (20e) on wall A and the airflows entering in through the apertures (20f, 20g) on wall B create an effective turbulence in the second part (20d) of the manifold. This turbulence disperses the agglomeration in the dry powder medicament entrained to the second part (20d) of the manifold and enables the medicament in dry powder form to be delivered to the patient at an appropriate particle size distribution.

Figure 5A:
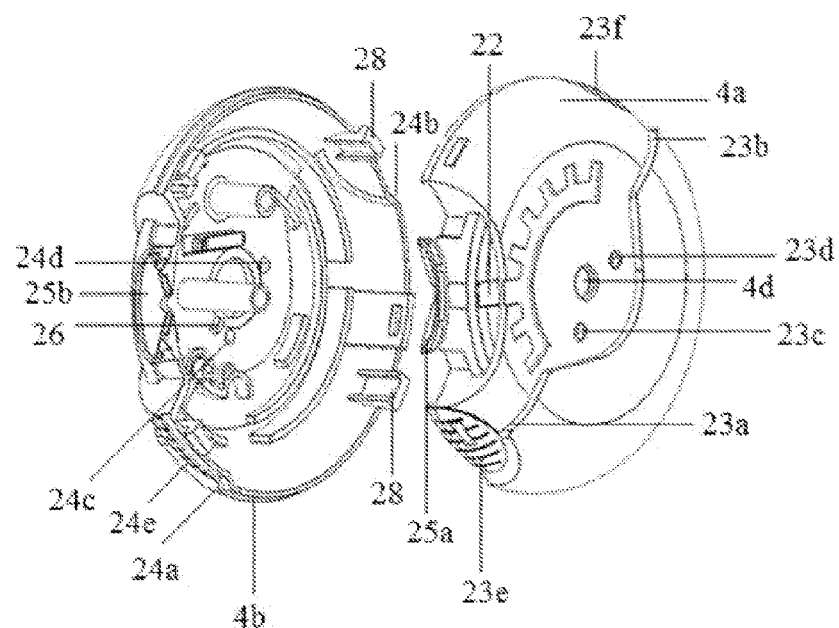
FIGS. 5a and 5b are perspective views of upper and lower housing members of the inhaler according to the invention, respectively.
Figure 5B:
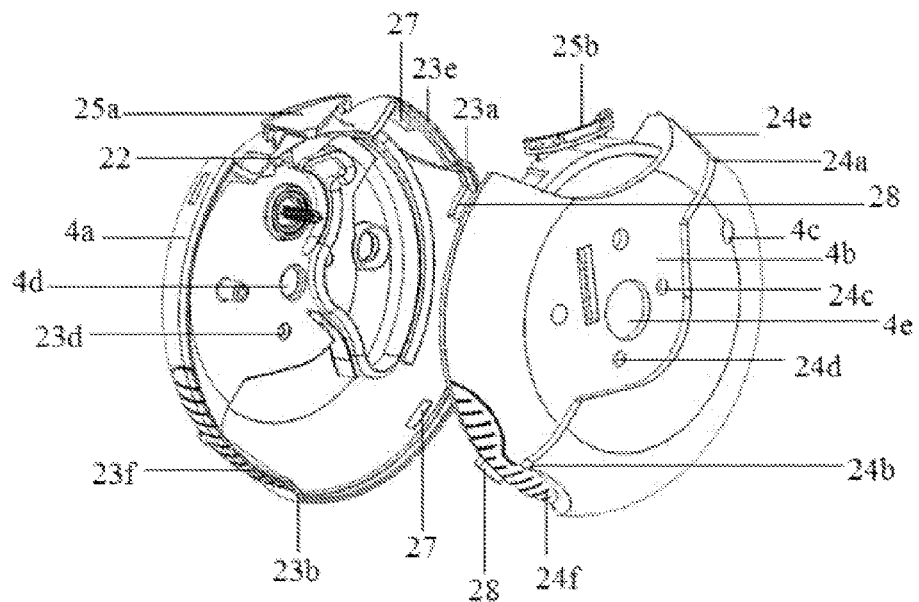
Figure 5C:
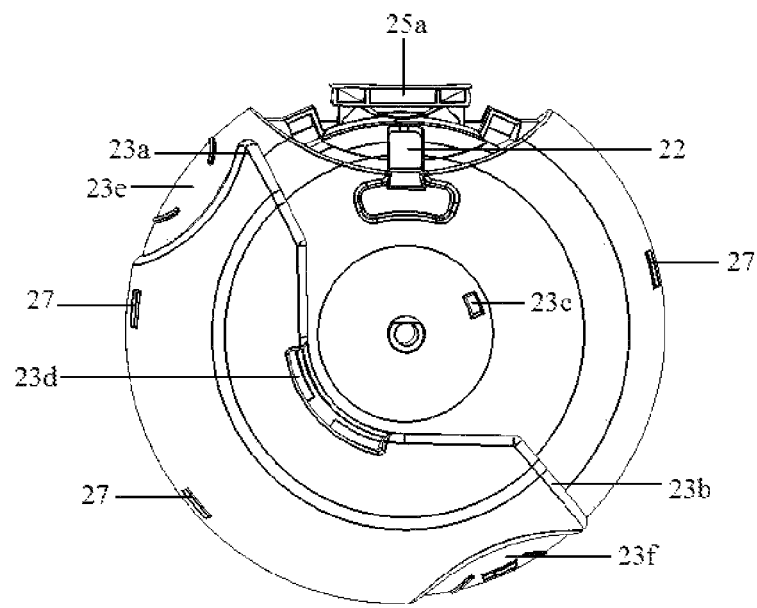
FIG. 5c is another perspective view of the upper housing member of the inhaler of the invention.
Figure 5D:
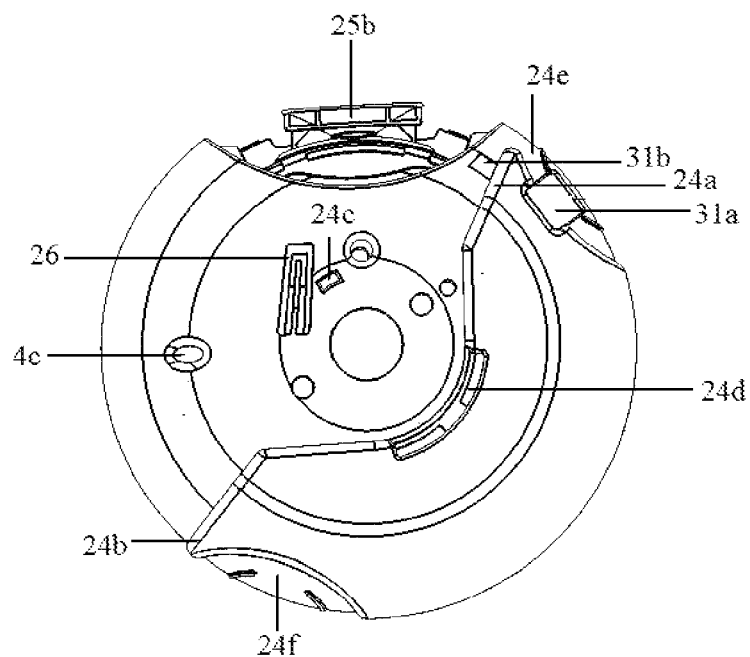
FIG. 5d is another perspective view of the lower housing member of the inhaler of the invention.
Figure 5E:
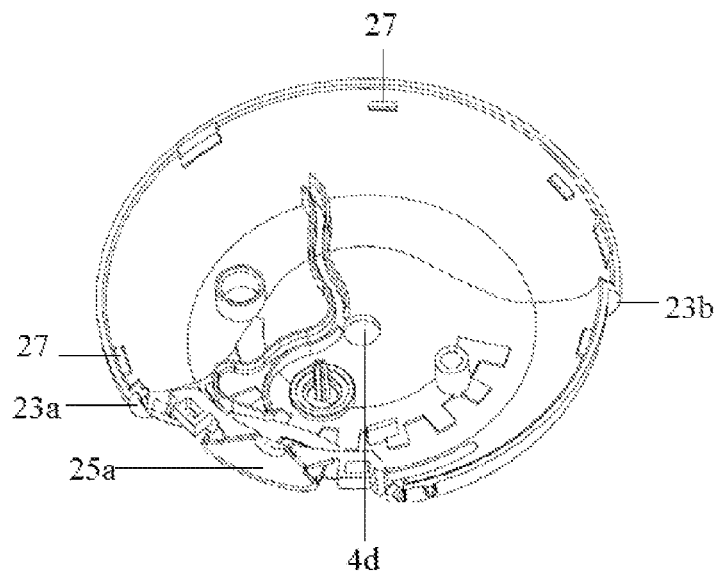
FIGS. 5e and 5f are perspective views of the inner and outer sides of the upper housing member of the inhaler according to the invention, respectively.
Figure 5F:
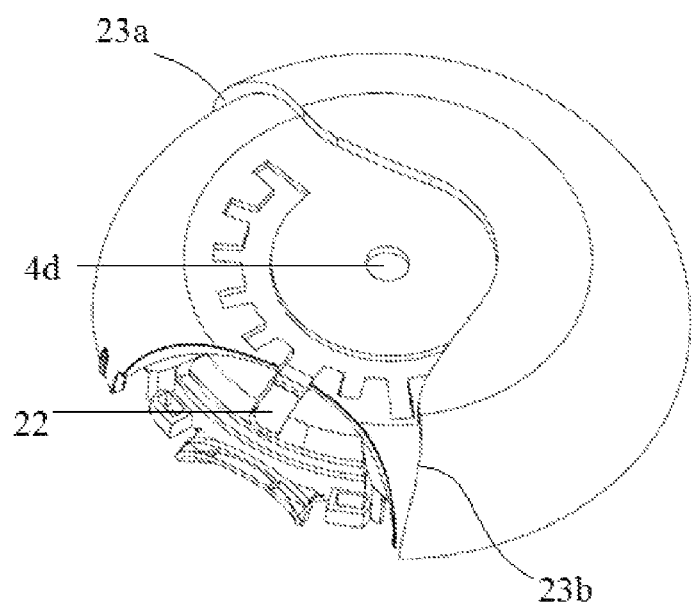
Figure 5G:
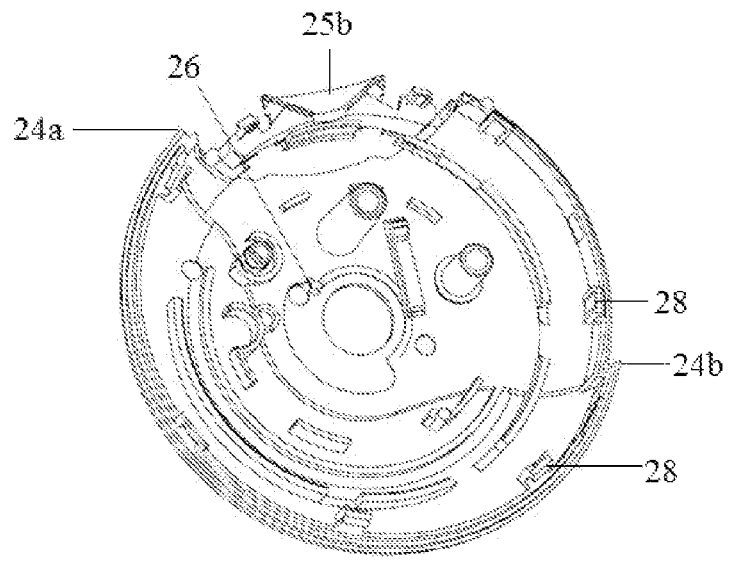
FIGS. 5g and 5h are perspective views of the inner and outer sides of the lower housing member of the inhaler according to the invention, respectively.
Figure 5H:
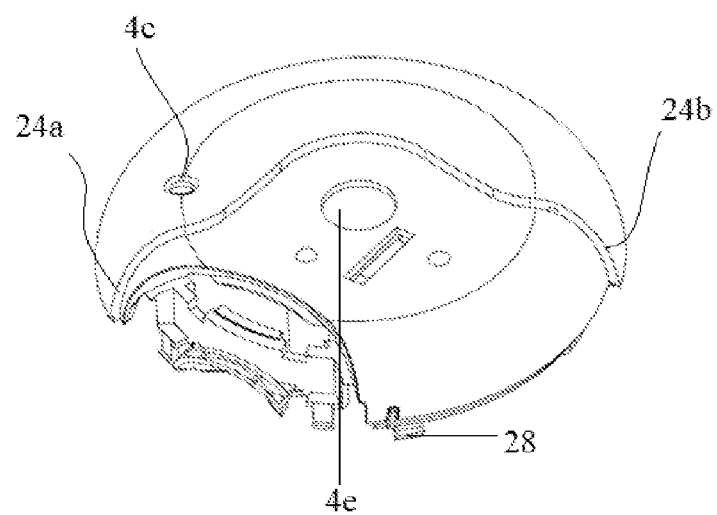
Figure 5I:
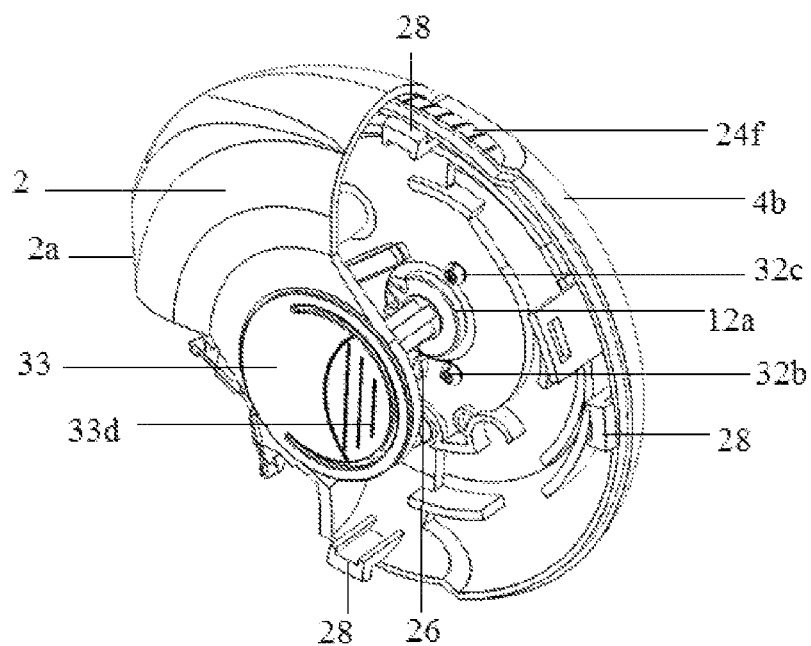
FIG. 5i is a cross-sectional view of the connection of the stabilizing resilient cover with the lower housing member in the inhaler pertaining to the invention.

The drive gear (12) passes through the aperture (4d) in the center of the upper housing member displayed in FIGS. 5e and 5f and the aperture (4e) in the center of the lower housing member, then it is joined with the mouthpiece cover (2) on two ends. There is a tapered channel between the manifold (20) and the mouthpiece (14). As displayed in FIGS. 5c and 5d, one half (25a) of the tapered channel that interconnects the manifold (20) that exist in the housing (10) with the mouthpiece (14) is comprised in the upper housing member (4a) while the other half of it (25b) is comprised in the lower housing member (4b). The channel is constituted as a whole when the upper (4a) and the lower (4b) housing members are joined together. Upon the inhalation of the patient, the air that enters the device through the air inlet (22) arranged in the upper housing member (4a) passes through the aperture with four sub-apertures (20a), reaches the opened blister (15a) and entrains the dry powder medicament there to the manifold (20) by passing it through the other aperture with four sub-apertures (20b). The grids on the upper housing member (23e, 230 and the grids on the lower housing member (24e, 240 prevent the slips of fingers when rotating the mouthpiece cover.

Figure 6A:
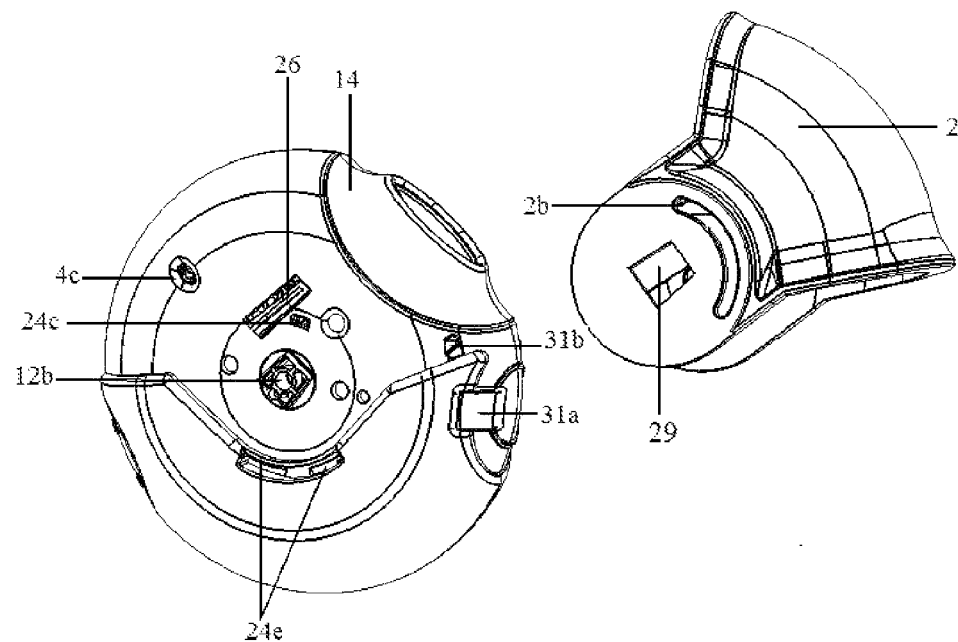
FIG. 6a is a view of the mouthpiece cover exploded from the inhaler.
Figure 6B:
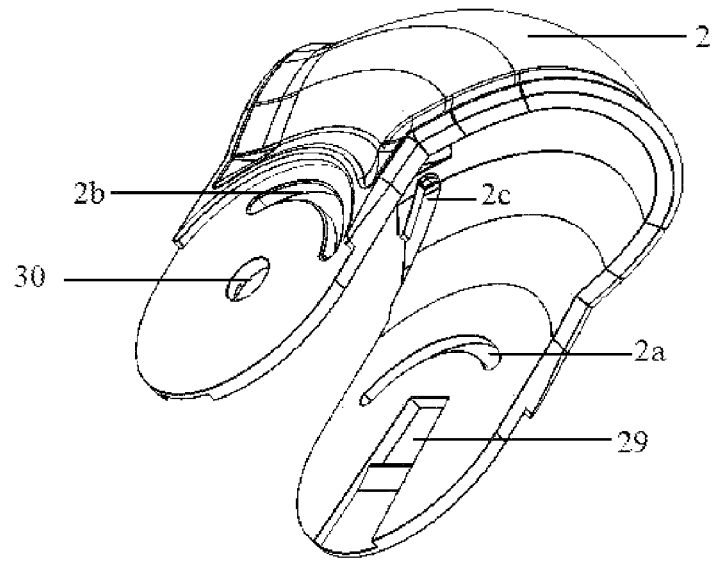
FIG. 6b is another perspective view of the mouthpiece cover of the inhaler of the invention.
Figure 6C:
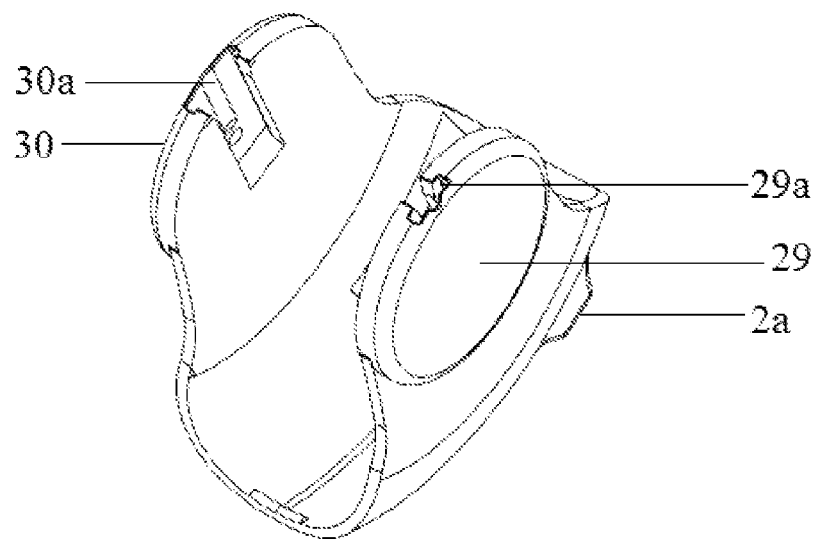
FIGS. 6c and 6d are perspective views of the inner and outer sides of the mouthpiece cover of the inhaler according to the invention, respectively.
Figure 6D:
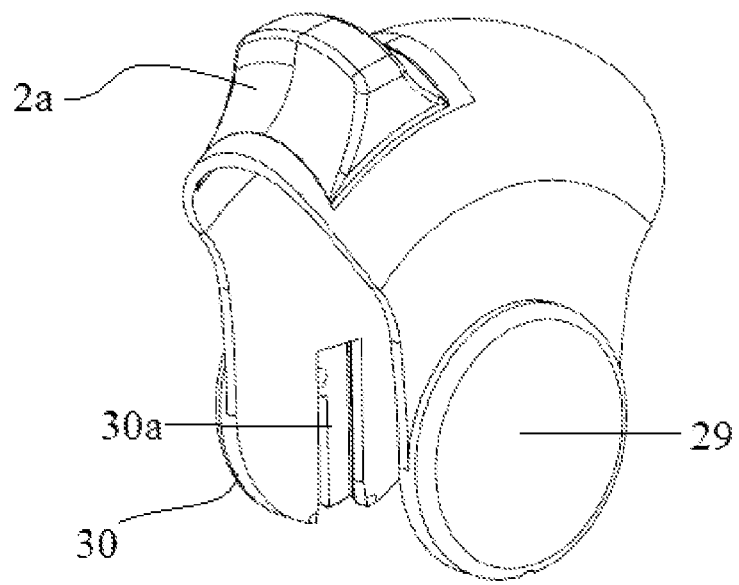
Figure 6E:
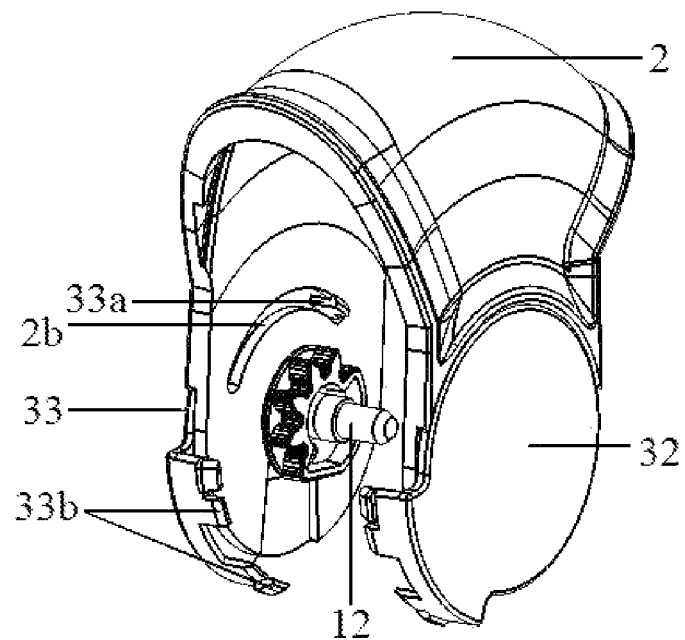
FIG. 6e is a perspective view of the connection between the mouthpiece cover, the drive gear, and the protective covers of the inhaler of the invention.
Figure 6F:
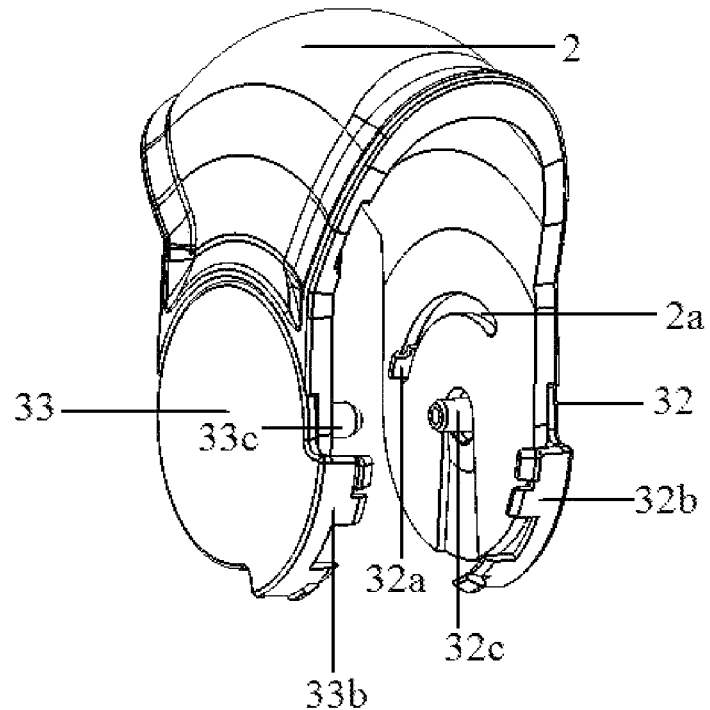
FIG. 6f is a perspective of the connection between the mouthpiece cover and the protective covers of the inhaler of the present invention.
Figure 6G:
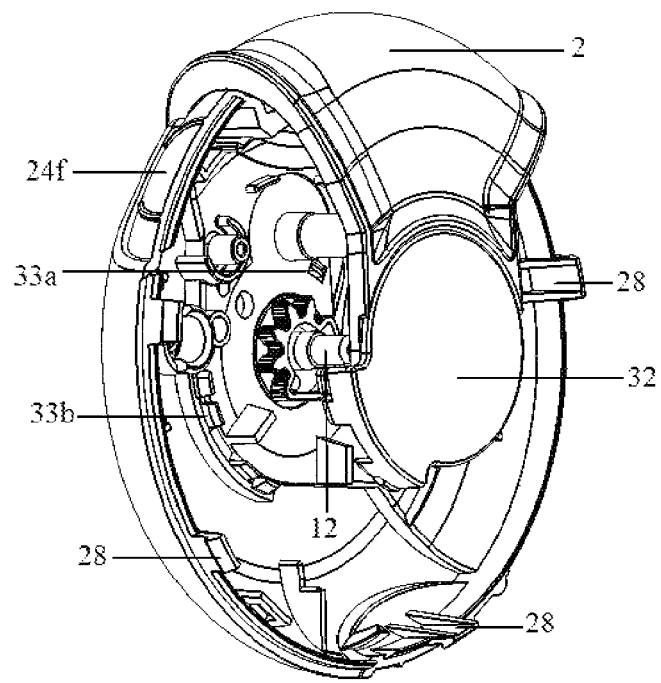
FIG. 6g is a perspective view of the connection between the mouthpiece cover, the drive gear, the lower housing member, and the protective cover of the inhaler of the present invention.
Figure 6H:
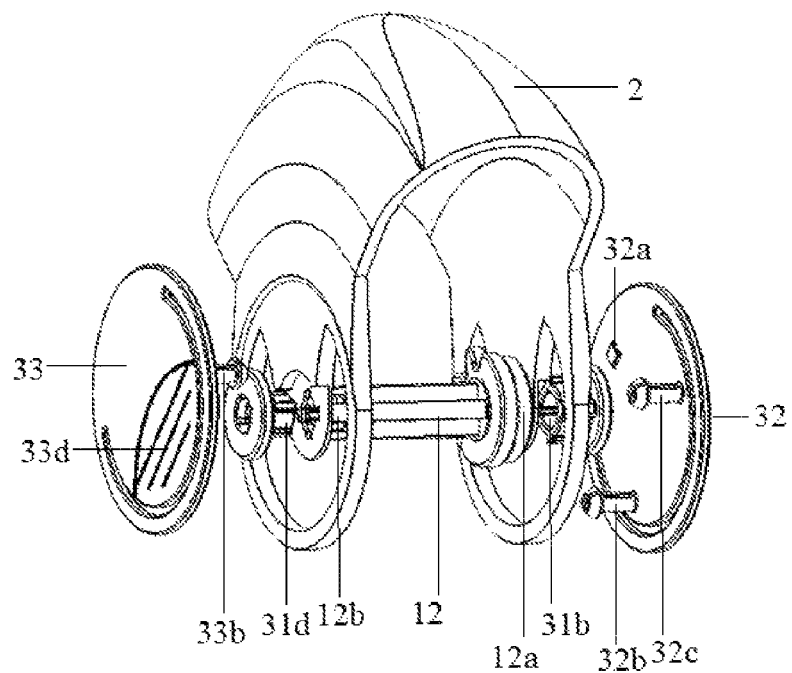
FIG. 6h is an exploded view of the communication between the mouthpiece cover, the drive gear and the stabilizing resilient covers in the inhaler according to the invention.

The mouthpiece cover (2) of the inhaler pertaining to the present invention is displayed in FIGS. 6a through 6f. The carved part, which is the finger tab (2a) in one end of the device enables the mouthpiece cover to be easily removed manually as seen in FIG. 6d. The finger tab (2a) has been designed to match the finger shape and is situated in any suitable spot on the mouthpiece cover (2). As can be seen clearly in FIGS. 6c and 6d, the first and the second connection points (29, 30) of the mouthpiece cover have recesses (29a, 30a) on their inside surfaces. Protrusions (31a, 31b) on the two ends of the drive gear (12) displayed in FIGS. 7e and 7f make a male-female connection with these recesses (29a, 30a). The first recess (30a) on the inside surface of the mouthpiece cover engages with the first protrusion (31a) on the one end of drive gear while the second recess on the inside surface of the mouthpiece cover (29a) engages with the second protrusion (31b) on the other end of the drive gear and the connection provided between each end of the drive gear (31a, 31b) and the corresponding recess (30a, 29a) on the inside surface of the mouthpiece cover is a male-female connection. The male-female connection that each end of the drive gear (31a, 31b) makes with the corresponding recessed parts on the inside surface of the mouthpiece cover (30a, 29a) causes to form an inside lock connection between the drive gear (12) and the mouthpiece cover (2) with maximum ±0.01% margin of error. Therefore, the rotational movement of the mouthpiece cover (2) on the upper (4a) and lower (4b) housing members is accurately transmitted to the indexing ratchet wheel by the drive gear (12) which has an inside lock connection with the mouthpiece cover (2) on its two ends.

The mouthpiece cover (2) is joined with the gear mechanism via the connection points. The drive gear consists of two ends (12a, 12b) and a hole (12c) at the center of one end as seen in FIG. 7g. Further, the drive gear (12) is joined with the connection points (29, 30) of the mouthpiece cover via the side covers (31a, 31c) as it can clearly be seen in FIGS. 6e, 6h, 6i and 6j illustrating the communication between the mouthpiece cover (2), the drive gear (12), side covers (31a, 31c) and the stabilizing resilient covers (32,33). Each of these side covers (31a, 31c) passes through the center (4d) of the upper housing member or the center (4e) of the lower housing member and joins with the end (12a, 12b) of the drive gear. It can clearly be seen in FIG. 6j that the both ends (12a; 12b) of the drive gear are carved such that the end of the side cover (31b, 31d) can pass through. The end of the drive gear (12a) that is fixed into one connection point (29) of the mouthpiece cover has a hole (12c) at the center. In addition, each of the connection points (29, 30) itself is a hole in shape (FIG. 6b). Therefore, the end of the drive gear (12a) is fixed into the connection point (29) of the mouthpiece cover while the extension part (33c) present at the centre of the inside surface of the protective cover is fixed into both the hole (12c) at the centre of said end of the drive gear and the connection point of the mouthpiece cover.

Figure 7A:
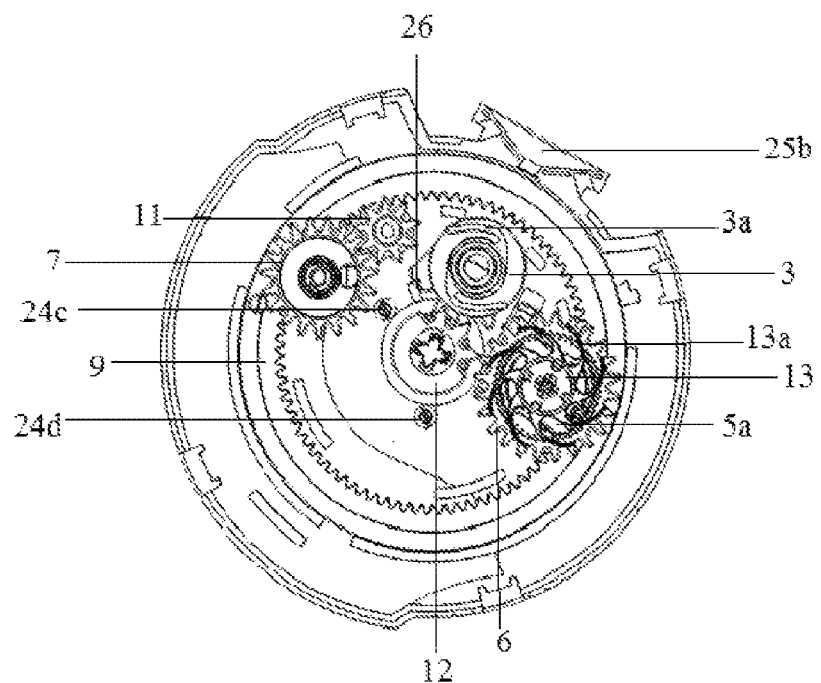
FIGS. 7a and 7b are cross-sectional views of the engagement of the gears composing the gear mechanism with each other in the inhaler according to the present invention.
Figure 7B:
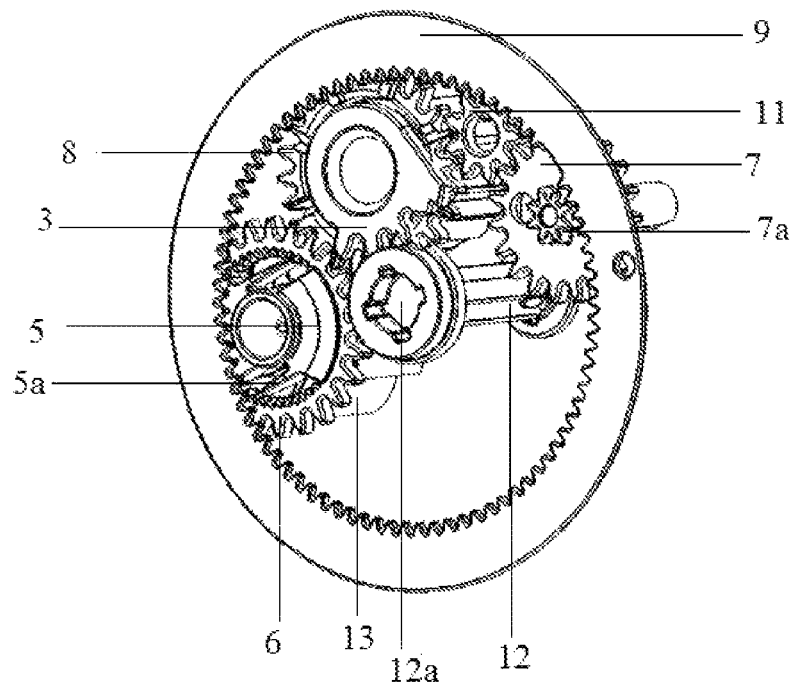
Figure 7C:
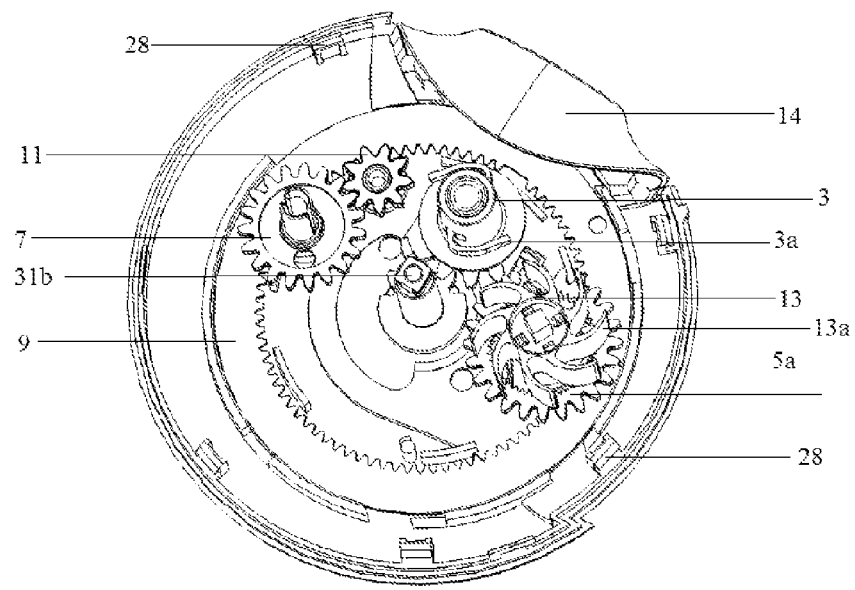
FIG. 7c is a cross-sectional view of the engagement of the gears composing the gear mechanism in the inhaler of the present invention.
Figure 7D:
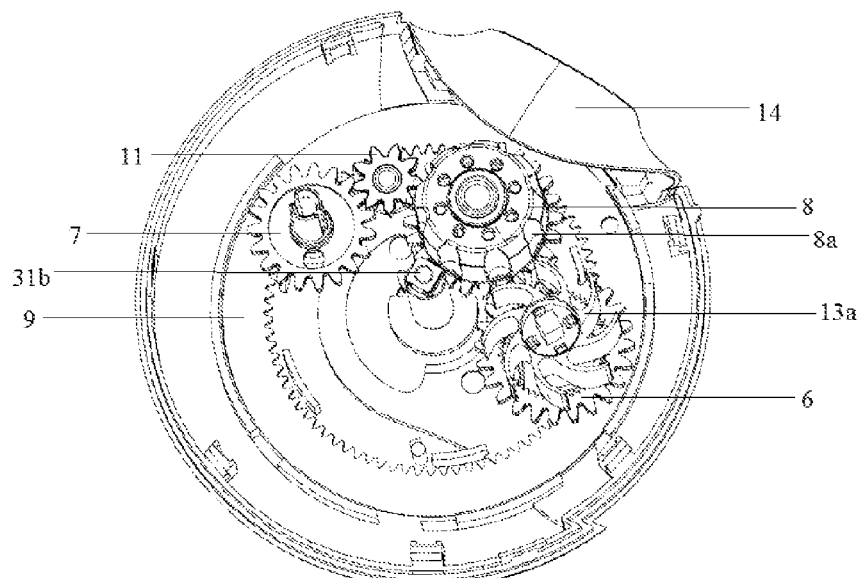
FIG. 7d is another cross-sectional view of the engagement of the gears composing the gear mechanism in the inhaler of the present invention.
Figure 7E:
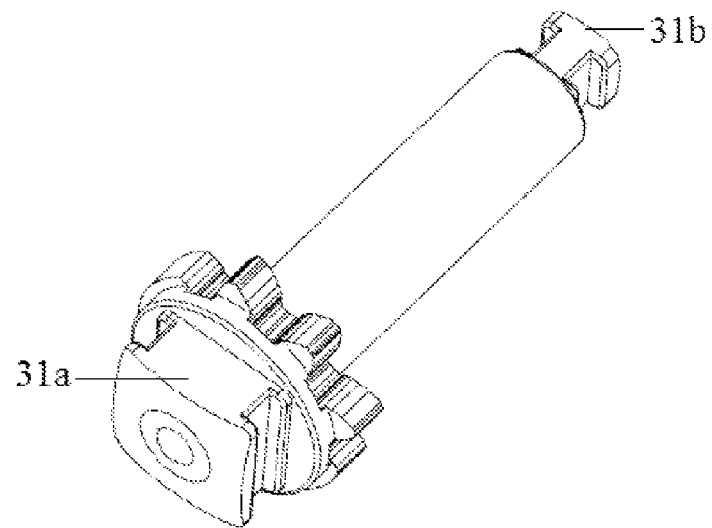
FIGS. 7e and 7f are perspective views of the drive gear of the inhaler according to the invention.
Figure 7F:
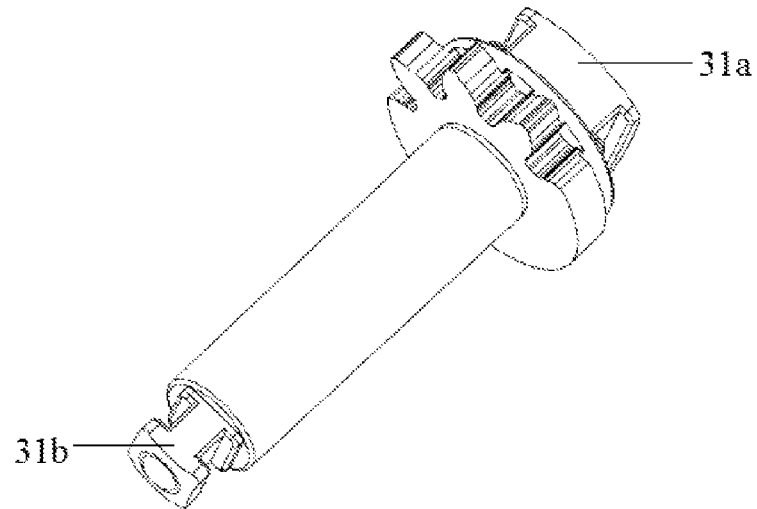

The shape of one connection point (29) of the mouthpiece cover is different from the shape of the second connection point (30) of the mouthpiece cover as well as the shape of the end of the drive gear (12a) that is connected with one connection point (29) of the mouthpiece cover is different from shape of other end of the drive gear (12b) (FIGS. 6b, 7f and 7g).

Each end of the side covers (31d, 31b) passes through one of the connection points (29, 30) of the mouthpiece cover and it is received in the recess in one end (12b, 12a) of the drive gear, thus it provides to tightly and stably interconnect the mouthpiece cover (2) with the drive gear (12). It is provided that the mouthpiece cover (2) synchronizes with the drive gear (12) as the connection point (29, 30) of the mouthpiece cover which has a matching shape with the ends (31d, 31b) of the side covers that passes through it on both sides of the device and the end (12b, 12d) of the drive gear that it communicates with are on the same component.

As is seen from FIGS. 6a through 6j, and 7h, the shapes of the ends (31b; 31d) of the side covers that are received in the carved parts on the ends of the drive gear and the shapes of the connection points (29, 30) of the mouthpiece cover are not identical since the two ends (12a, 12b) of the drive gear are not identical.

The mouthpiece cover (2) rotates by the same angle each time it is switched from the first position to the second position on the path restricted by the protrusions (29a, 29b, 30a, 30b) on the upper and the lower housing members (4a, 4b). The rotational angle of the mouthpiece cover (2) varies depending on the shape and the size of the device but is a fixed value between 30° and 160°. This angle is adjusted according to the shape and the size of the device such that the indexing wheel (8) having 8 recesses (8a) rotates 45 degrees in response to each actuation of the device. The mouthpiece cover (2) rotates by the same angle on its two ends in response to each actuation of the device and this rotational movement of the mouthpiece cover (2) is accurately transmitted to the indexing wheel (8) by the indexing ratchet wheel (3) because of the drive gear (12) which is tightly attached to the mouthpiece cover (2) and the indexing wheel is provided to rotate 45° each time the device is triggered.

Figure 2C:
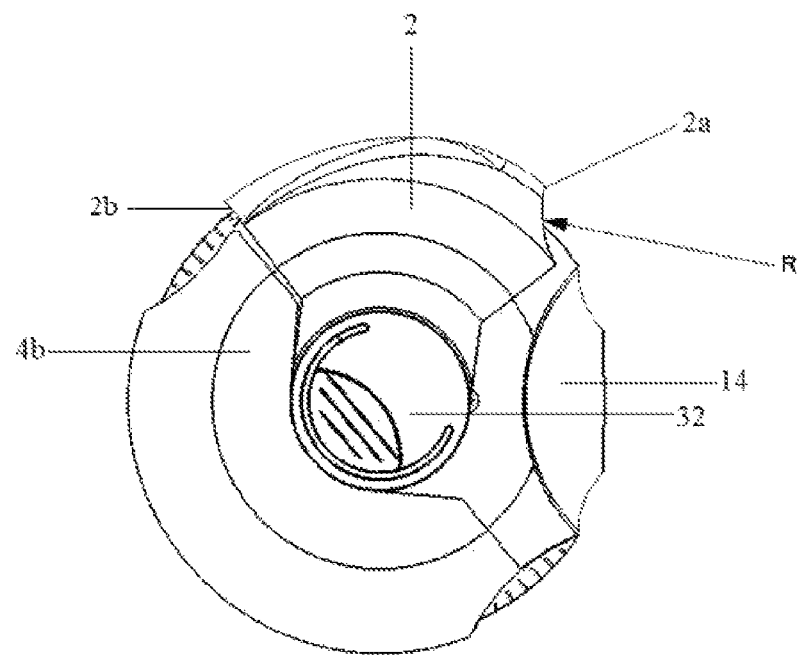
FIG. 2c is a front view of the inhaler according to the present invention.

The mouthpiece cover (2) can be rotated by holding from the front end (2a) or back end (2b) of its with the help of the thumb. Therefore, the front end (2a) or the back end (2b) of the mouthpiece cover (2) is in contact with the patient's finger while it is moved manually. According to FIG. 2c, only the front end (2a) of the mouthpiece cover (2) of the inhaler is carved such that it matches with the shape of the thumb so as to provide the mouthpiece cover (2) to be rotated easily and rapidly while the back end (2b) of the mouthpiece cover is not carved. However, it is probable that both the front end (2a) and the back end (2b) of the mouthpiece cover are carved. The shape of the carved part in the front end (2a) of the mouthpiece cover resembles to the shape of the thumb for the thumb to be placed in this carved part exactly in order to rotate the mouthpiece cover. Thus, the carved part of the front end (2a) of the mouthpiece cover illustrated in FIG. 2c is in the shape of the arc of the circle which has a radius (R) in the range of 30 mm to 40 mm, preferably in the range of 32.5 mm to 37.5 mm. In more detail, the carved part (2a) in the front end of the mouthpiece of the device shown in FIG. 2c is in the shape of the arc of 45° of said circle.

Figure 2D:
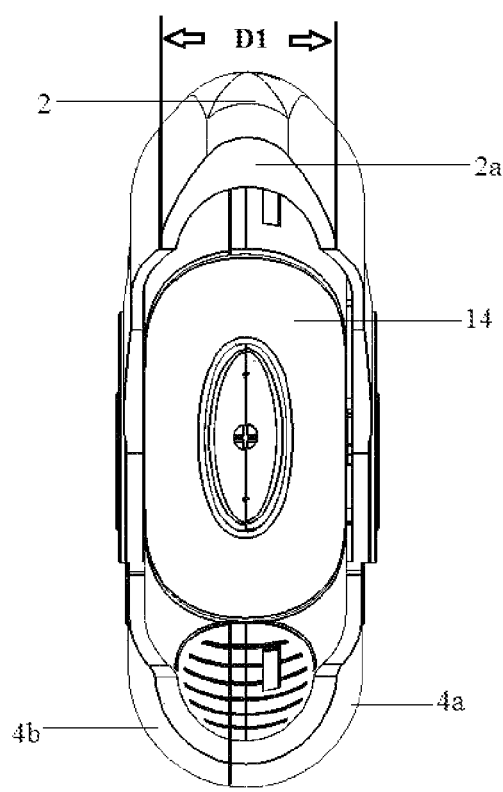
FIG. 2d is a lateral view of the inhaler according to the present invention.

In addition, another variable contributing to the carved part in the front end (2a) of the mouthpiece cover to match with the shape of the thumb is the width of the mouthpiece cover (2) illustrated as D1 in FIG. 2d. For the thumb to be able to grip the cover and impose force, a particular part has to be in contact with the carved part in the front end (2a) and the back end (2b) of the mouthpiece cover. To this end, D1 distance is in the range of 10 mm to 20 mm, preferably in the range of 11 mm to 16 mm.

Figure 8:
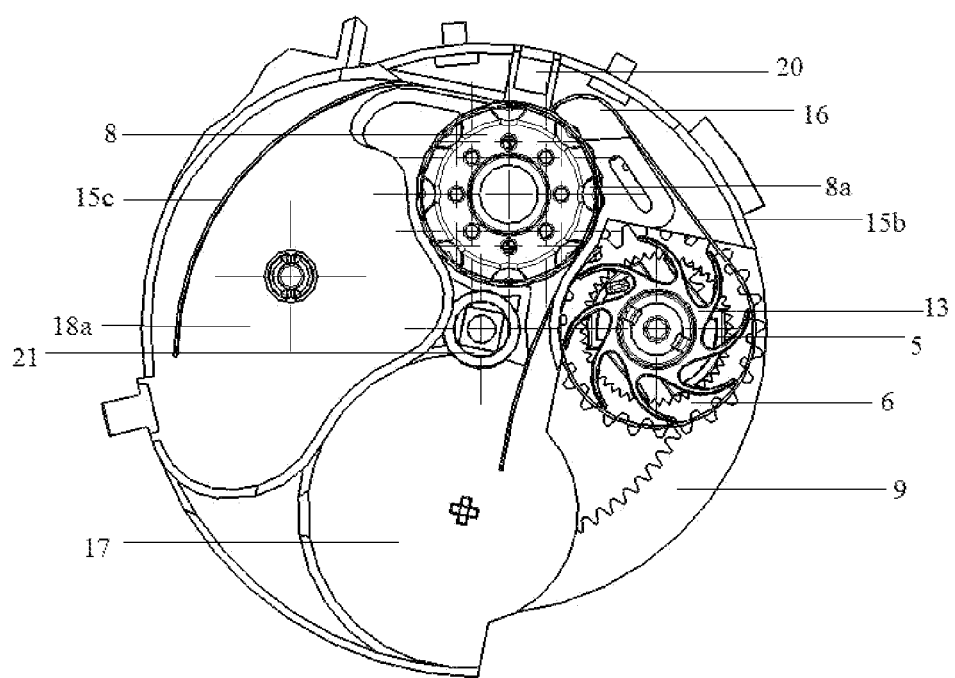
FIG. 8 is a cross-sectional view of the blister package delaminating in course of operation of the inhaler according to the present invention.

There are 8 recesses (8a) on the indexing wheel displayed in FIG. 2a and the indexing wheel (8) rotates 45° each time for the blisters received in these recesses to be able to be positioned accurately. The blister package (15) is indexed by the 45° rotation of the indexing wheel (8) in response to each actuation of the device and is peeled by the beak (16) so one dose of the dry powder medicament becomes ready for inhalation when one blister pocket is opened. As seen in FIG. 8, the lid sheet (15b) that is peeled away by the beak (16) and the base sheet (15c) of the blister package (15) are enclosed in separate compartments. The lid sheet (15b), which provides impermeability of the blister package, passes over the beak (16) and tightly coils on the wings (13a) of the winding wheel. The base sheet (15c) with blister pockets (15a), each of which comprises one dose of the dry powder medicament, is accumulated in the separated compartment (18a) in the housing (10). In response to each actuation of the inhaler (1), one dose of the dry powder medicament becomes ready for inhalation after one blister pocket (15a) is opened; the air which enters the device through the air inlet (22) upon the inhalation of the patient entrains the dry powder medicament to the mouthpiece and provides to deliver it to the patient.

Figure 6I:
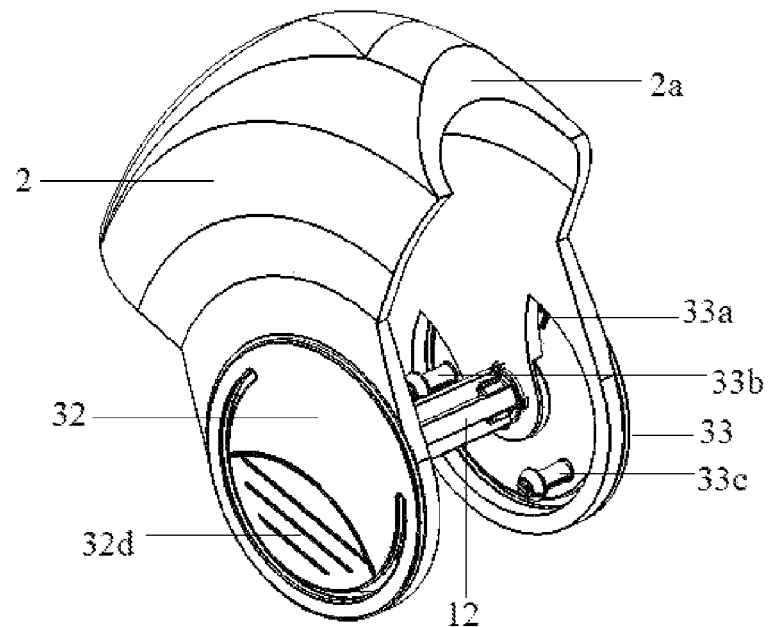
FIG. 6i is a cross-sectional view of the communication between the mouthpiece cover, the drive gear and the stabilizing resilient covers in the inhaler according to the invention.
Figure 6J:
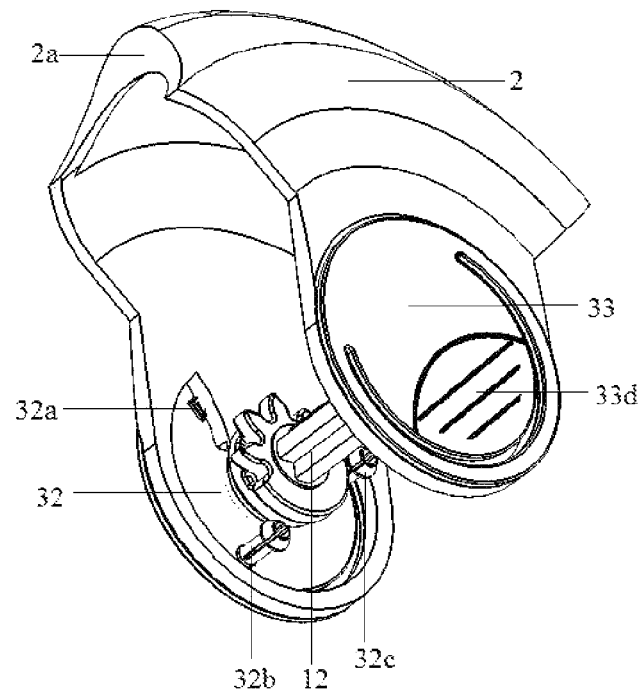
FIG. 6j is a cross-sectional view of the communication between the mouthpiece cover, the drive gear and the stabilizing resilient covers in the inhaler according to the invention.
Figure 7G:
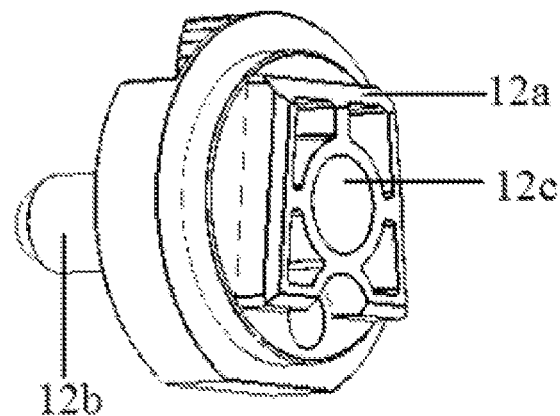
FIG. 7g is a perspective view of the drive gear of the inhaler of the invention.
Figure 7H:
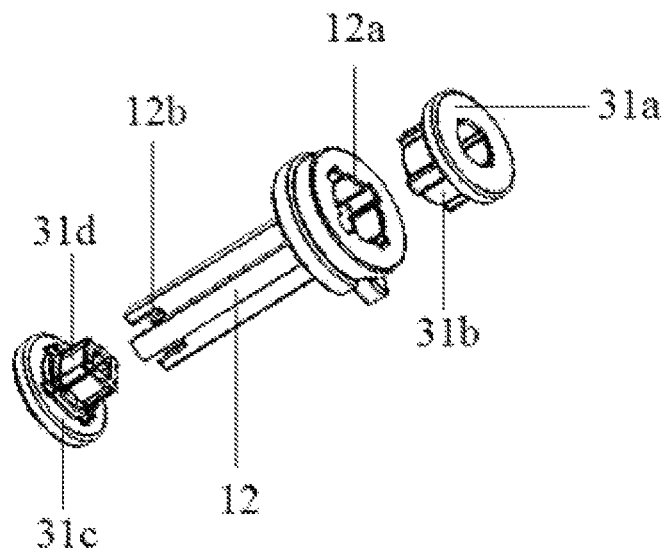
FIG. 7h is an exploded view of the communication between the drive gear and the side covers in the inhaler according to the invention.

There is one stabilizing resilient cover (33; 32) on each connection point (29; 30) of the mouthpiece and on each side cover (31c; 31a), as displayed in FIGS. 2a, 6a, 6h-6j and 5i. When the mouthpiece cover (2) is in the first position, the pawls (32a, 33a) under the stabilizing resilient covers, which are on the connection points (29, 30) of the mouthpiece, interlock with the mouthpiece cover (2) on both sides as clearly seen in FIGS. 6i and 6j. The pawl (33a) under the stabilizing resilient cover that is on the first connection point (29) interlocks with the mouthpiece cover on one side (FIG. 6i). Identically, the pawl (32a) under the stabilizing resilient cover that is on the second connection point (30) of the mouthpiece cover interlocks with the mouthpiece cover (2) on the other side (FIG. 6j). Thus, these pawls (32a, 33a) under the stabilizing resilient covers prevent the movement of the mouthpiece cover (2) by interlocking with it on both sides.

The extensions (32b, 32c, 33b, 33c) under the stabilizing resilient covers pass through the apertures (23c, 23d, 24c, 24d) on the upper and the lower housing members illustrated in FIGS. 5a and 5b and provide the stabilizing resilient covers to remain stable. Namely, the extensions (33b, 33c) under the stabilizing resilient cover that is on the first connection point (29) of the mouthpiece cover pass through the apertures (23c, 23d) on the upper housing member and provide one of the stabilizing resilient covers (33) to be stably joined with the device. Identically, the extensions (32b, 32c) under the stabilizing resilient cover on the second connection point (30) of the mouthpiece cover pass through the apertures (24c, 24d) on the lower housing member and provide one of the stabilizing resilient covers (32) to be stably joined with the device as clearly illustrated in FIG. 5i.

Before the inhalation, the resilient parts (32d, 33d) of each stabilizing resilient cover illustrated in FIGS. 6i and 6j are pressed on for raising the pawls (32a, 33a) and releasing the mouthpiece cover (2) in order to actuate the gear mechanism of the device to prepare one dose of dry powder medicament before inhalation. Therefore, the gear mechanism of the device is actuated and one blister pocket (15a) is opened for one dose of the dry powder medicament to be ready for inhalation when the resilient parts (32d, 33d) of the stabilizing resilient covers are pressed on and the mouthpiece cover (2) is switched from the first position to the second position simultaneously. The necessity to press on the resilient parts (32d, 33d) of the stabilizing resilient covers so as to actuate the gear mechanism preclude the consequences which may result from accidental and inadvertent actuations of the gear mechanism.

Another aspect of the present invention, a stopper can attach to the top cover of said dry powder inhaler to engage the movable mouthpiece cover for providing irreversible movement of said mouthpiece cover as well as it also engages the index gear interacting with the index wheel after the advancement of the peelable blister strip. In each actuation of the dispensing mechanism, the movement of the mouthpiece cover from one position, in which the mouthpiece is completely uncovered, to another position, in which the mouthpiece is completely closed, results in the advancement of the peelable blister strip to the same extent. The stopper which engages the movable mouthpiece cover to prevent its reversible movement from the position in which the mouthpiece is completely uncovered and open blister of the peelable blister is situated correctly for an effective inhalation of the dry powder medicament from opened blister. Also, the stopper which is attached to the top cover of said dry powder inhaler, make it possible to prevent reversible rotation of the index wheel undirectly because of the fact that the movable mouthpiece cover is attached directly to the dispensing mechanism through the center of the dry powder inhaler.

Figure 4I:
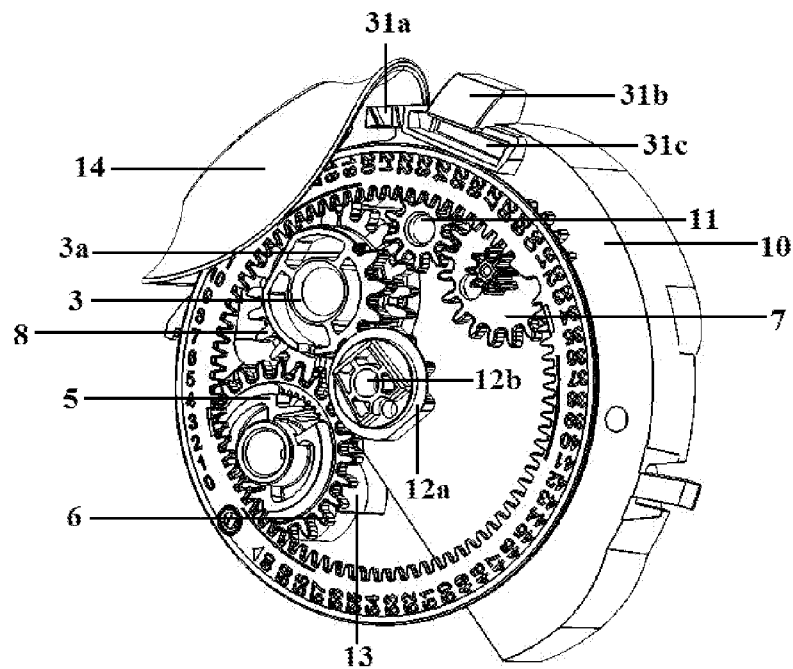
FIGS. 4i and 4j are perspective views of the housing and the gear mechanism of the inhaler of the invention.
Figure 4J:
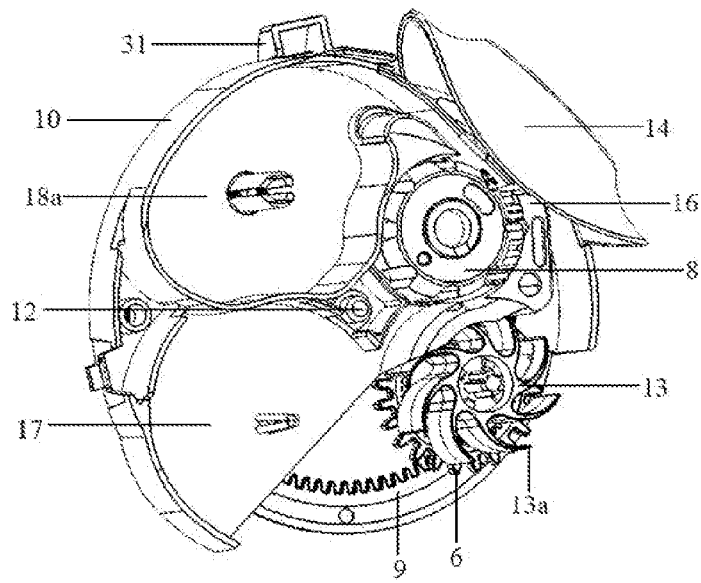
Figure 10A:
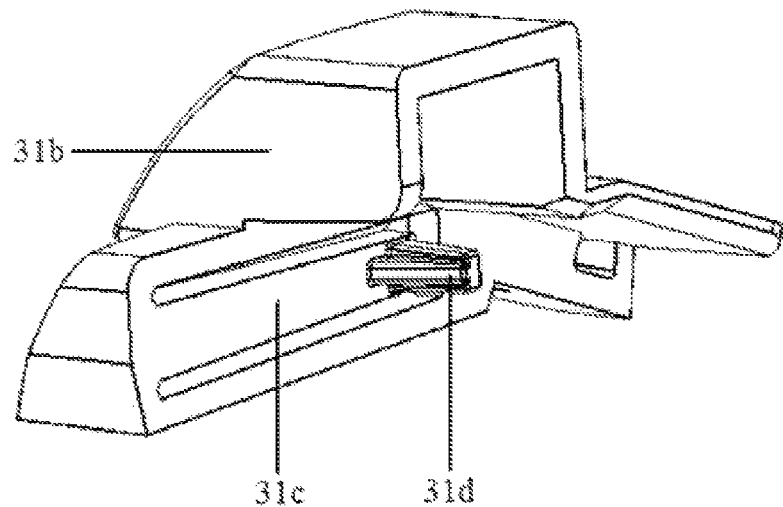
FIGS. 10a and 10b are perspective views of the stopper consisting of the pawl, the pressing button, and the supporting member used in the inhaler of the present invention.
Figure 10B:
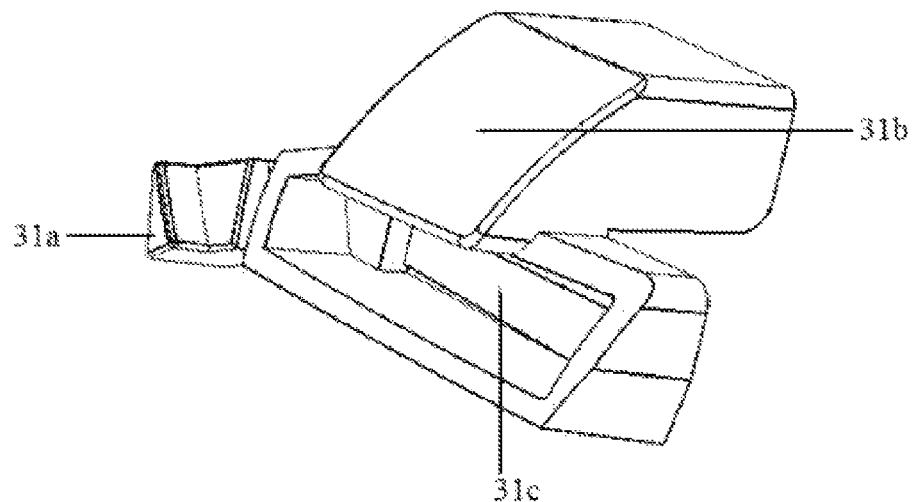

The inhaler (1) of the present invention has a stopper (31) that is situated between the lower housing member (4b) and the housing (10) as engaging with the two holes on the lower housing member (4b) (FIGS. 5d and 6a). The stopper is shown in FIGS. 10a and 10b. This stopper (31) consists of a pawl (31a), a pressing button (31b), and a supporting part (31c). Each of the pawl (31a) and the pressing button (31b) situated in one hole of the lower housing member (4b) and is shown from the outside as the supporting part (31c) is situated at the inside of the inhaler and is not shown from the outside (FIGS. 4i and 6a). For actuation of the inhaler, the mouthpiece cover (2) is switched from the first position to the second position over the rotational path. However, the pawl (32a) is engaged to the recess part (2c) on inside surface of the mouthpiece cover (2) to prevent the movement of the mouthpiece cover (2) when the mouthpiece cover (2) is in the first position in which the mouthpiece (14) is completely covered. Since the pressing button (31b) moves synchronously with the pawl (31a), when the pressing button (31b) is pressed, the pawl (31a) is advanced forward inside of the inhaler and disengaged from the mouthpiece cover (2). After the pawl (31a) is disengaged from the mouthpiece cover (2), the mouthpiece cover (2) can be rotated from the first position to the second position to actuate the inhaler.

Because of the supporting part (31c) of the stopper, there is no need for a spring to enable the pressing button (31b) to be pressed. There is an end (31d) that is integrated with the supporting part and leans the housing of the inhaler. When the pressing button is pressed, the supporting part springs over the end of said supporting part (31d) and both of the pressing button (31b) and the pawl (31a) are advanced forward inside of the inhaler.

Figure 11:
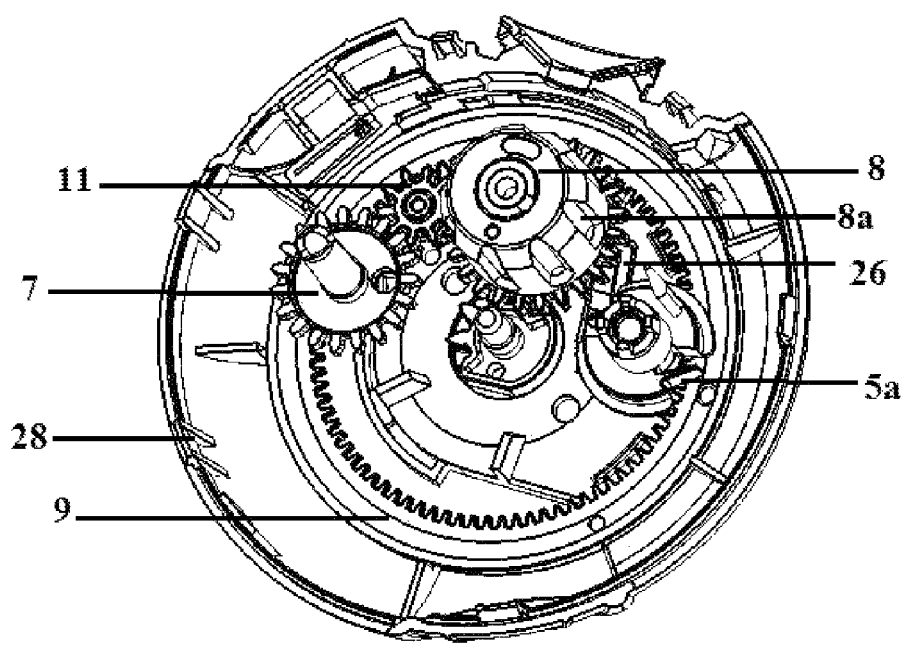
FIG. 11 is a perspective view of the connection between the indexing wheel and another stopper used in the inhaler of the invention.

The inhaler has another stopper (26) in the lower housing member (4b) in order to provide the opened blister in the blister package (15) which is indexed by the indexing wheel (8) to be positioned precisely. FIGS. 7a, 7b, and 11 show that the stopper (26) interlocks with the tooth of the indexing wheel (8) and hinders its rotation. The rotational movement of the mouthpiece cover (2) by the same angle each time the inhaler (1) is actuated is precisely transmitted to the indexing ratchet wheel (3) by the drive gear (12) that joins with one connection point (29) of the mouthpiece cover, and therefore the indexing wheel (8) which engages with the indexing ratchet wheel (3) is rotated by the same angle each time the inhaler (1) is actuated. The stopper (26) positioned in the lower housing member (4b) prevents backward movement of the blister package (15) which is indexed by the indexing wheel (8) that synchronizes with the indexing ratchet wheel (3) by keeping the position of the indexing wheel (8) stable and provides the blister package (15) to be precisely positioned.

As can be seen in FIGS. 7a through 7c, the indexing wheel (8) which synchronizes with the indexing ratchet wheel (3) is engaged with the winding wheel gear (6) and the pinion gear (11) and the rotation of the indexing wheel (8) causes the pinion gear (11) and the winding wheel gear (6) to rotate. Thus, both the peeled lid sheet (15b) of the blister package (15) which is indexed by the rotation of the indexing wheel (8) is tightly coiled on the winding wheel (13) engaging with the winding wheel gear (6) and also the counter gear (9) is provided to be moved by the pinion gear (11) and the base gear (7) as a result of the rotation of the indexing wheel (8).

Figure 9:
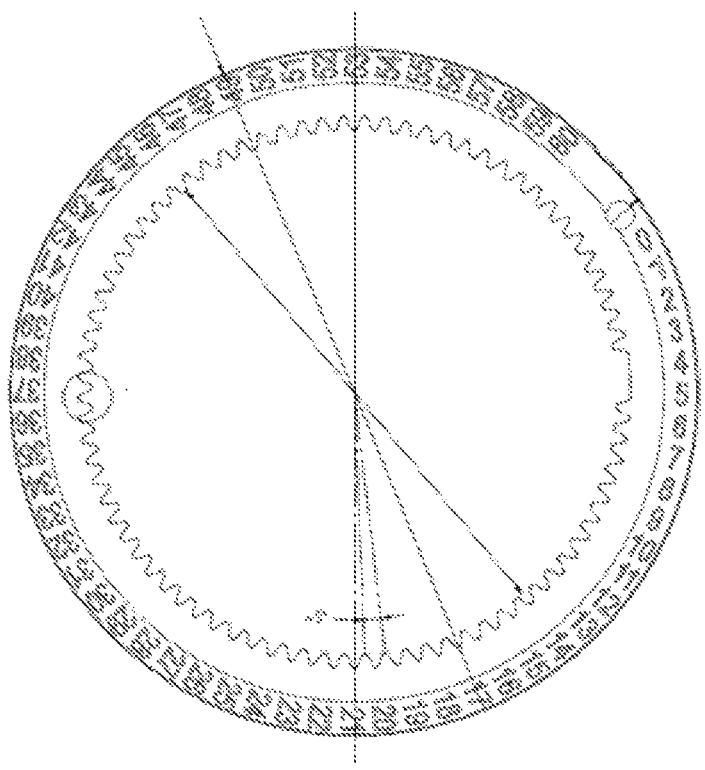
FIG. 9 is a perspective view of the counter gear used in the inhaler according to the present invention.

The rotation of the indexing wheel (8) is transmitted to the base gear (7) engaging with the pinion gear (11) by the pinion gear (11). The small gear which is under the base gear (7) as attached engages with the counter gear (9) (FIG. 7b). Thus, the movement of the indexing wheel (8) is transmitted to the counter gear (9) shown in FIG. 9 by the pinion gear (11) and the base gear. There are numerals incrementing from 1 to 60 in the counter gear displayed in FIG. 9. In response to each actuation of the device, the counter gear rotates approximately 5° and the number of unused blister pockets remained in the device are seen through the display aperture (4c) on the lower housing member (4b).

In use of the device described in FIGS. 1-12, the mouthpiece (14) is exposed when the mouthpiece cover (2) is slid from the first position to the second on the upper housing member (4a) and the lower housing member (4b); the gear mechanism is triggered by the drive gear (12) and one dose of dry powder medicament is prepared for inhalation; the counter gear (9) is indexed and the numeral seen through the display aperture (4c) on the lower housing member (4b) is incremented. After the inhalation is realized, the mouthpiece cover (2) is solely moved from the second position to the first position wherein the mouthpiece (14) is completely covered.

The medicament in dry powder form which is stored in blister cavities is manufactured according to the prior art. According to the present invention, the particle sizes of the active agents comprised in the dry powder medicament are smaller than 20 μm, preferably smaller than 10 μm.

The inhaler pertaining to the present invention has been designed so as to deliver the dry powder medicament used in monotherapy or combined therapy. The term "monotherapy" refers to inhalation treatments in which dry powder medicaments comprising a single active agent are used whereas the term "combined therapy" refers to inhalation treatments in which dry powder medicaments comprising more than one active agents are use used.

The dry powder medicament delivered via the device pertaining to the present invention comprises at least one excipient in addition to the active agent or agents. These excipients are generally chosen from a group comprising monosaccharides (glucose, arabinose, etc.), disaccharides (lactose, saccharose, maltose, etc.), oligo- and polysaccharides (dextran, etc.), polyalcohols (sorbite, mannite, xylite), salts (sodium chloride, calcium carbonate, etc.) or combinations thereof. According to the present invention, the medicament in dry powder form comprises lactose as the excipient. The medicament in dry powder form comprises fine or coarse excipients particles preferably having various particle size ranges in order to deliver the required amount to the lungs.

The active agent or the active agents comprised in the dry powder medicament which is stored in blister packages used in the device pertaining to the present invention can be selected from a group comprising cromolyns, anti-infectives, antihistamines, steroids, anti-inflammatories, bronchodilators, leukotirene inhibitors, PDE IV inhibitors, antitussives, diuretics, anticholinergics, hormones, xanthines and pharmaceutically acceptable combinations thereof.

The active agent comprised in the medicament in dry powder form delivered via the inhaler pertaining to the present invention is preferably selected from a group comprising tiotropium, oxitropium, flutropium, ipratropium, glicopironium, flunisolid, beclomethasone, budesonide, fluticasone, mometasone, ciclesonide, rofleponide, dexamethasone, montelukast, methylcyclopropane acetic acid, sodium cromoglicat, nedocromil sodium, Npropylene, teophylline, roflumilast, ariflo (cilomilast), salmeterol, salbutamol, formoterol, terbutaline, carmoterol, indacaterol, cetirizine, levocetirizine, efletirizine, fexofenadine and their racemates, free base, enantiomers or diastereomers and their pharmaceutically acceptable salts, solvates and/or hydrates or a combination of said active agents.

The device pertaining to the present invention is used in the administration of the medicament in dry powder form which is utilized in the treatment of respiratory diseases, particularly in asthma, chronic obstructive pulmonary disorder (COPD) and allergic rhinitis. Accordingly, the respiratory diseases include, but not restricted to, allergic or non-allergic asthma at any phases, acute lung injury (ALI), acute respiratory distress syndrome (ARDS), exacerbation of airways hyperactivity, bronchiectasis, chronic obstructive pulmonary including emphysema and chronic bronchitis, airways or lung diseases (COPD, COAD or COLD), pneumoconiosis, aluminosis, anthracosis, asbestosis, chalicosis, ptilosis, siderosis, silicosis, tabacosis and byssinosis. The device pertaining to the invention can be used in prophylactic or symptomatic treatment. In addition, the medicament in dry powder form which is preferably used in the symptomatic treatment of allergic asthma and COPD is administered to the patient via the device pertaining to the present invention.

What is claimed is:

1. An inhaler suitable for delivery of a medicament in dry powder form, wherein said medicament is carried by an elongate, peelable blister strip, characterized in that:
   the inhaler has a dispensing mechanism which is actuated by the movement of a mouthpiece cover;
   each blister of the elongate, peelable blister strip in which medicament in dry powder form is contained is opened by single movement of the mouthpiece cover; and
   the inhaler comprises a stopper for preventing reversible rotation of the elongate, peelable blister strip, thus providing a correct position for opening of the blister of the elongate, peelable blister strip
   the stopper ensures the elongate, peelable blister strip is in a correct and accurate position, and wherein the stopper is placed in the exterior of the dry powder inhaler beneath the mouthpiece cover when the mouthpiece is completely uncovered.

2. The inhaler of claim 1, wherein the stopper ensures that the mouthpiece cover is in a correct and accurate position for effective inhalation.

\* \* \* \* \*